(12) United States Patent
Kirkby et al.

(10) Patent No.: US 9,341,919 B2
(45) Date of Patent: May 17, 2016

(54) METHODS AND APPARATUS FOR CONTROLING DRIVE FREQUENCIES OF ACOUSTO-OPTIC DEFLECTORS

(75) Inventors: Paul A. Kirkby, Old Harlow (GB); K. M. Naga Srinivas Nadella, London (GB); R. Angus Silver, London (GB)

(73) Assignee: UCL BUSINESS PLC, London (GB)

( * ) Notice: Subject to any disclaimer, the term of this patent is extended or adjusted under 35 U.S.C. 154(b) by 502 days.

(21) Appl. No.: 13/642,151

(22) PCT Filed: Apr. 20, 2011

(86) PCT No.: PCT/GB2011/000608
§ 371 (c)(1),
(2), (4) Date: Feb. 1, 2013

(87) PCT Pub. No.: WO2011/131933
PCT Pub. Date: Oct. 27, 2011

(65) Prior Publication Data
US 2013/0148188 A1    Jun. 13, 2013

(30) Foreign Application Priority Data

Apr. 21, 2010    (GB) .................................. 1006679.3

(51) Int. Cl.
*G02B 26/08*    (2006.01)
*G02F 1/29*    (2006.01)
(Continued)

(52) U.S. Cl.
CPC .............. *G02F 1/33* (2013.01); *G02B 21/0036* (2013.01); *G02B 21/16* (2013.01); *G02B 26/08* (2013.01); *G01N 21/6458* (2013.01)

(58) Field of Classification Search
CPC .............. G02F 1/11; G02F 1/33; G02F 1/332

USPC .................................. 359/305, 310, 285–287
See application file for complete search history.

(56) References Cited

U.S. PATENT DOCUMENTS 3,944,948 A    3/1976 Redman et al.
4,217,036 A    8/1980 Chang
(Continued)

FOREIGN PATENT DOCUMENTS

EP    0485191    5/1992
EP    0620468    10/1994
(Continued)

OTHER PUBLICATIONS

International Search Report for PCT/GB2012/050824, mailed Jun. 22, 2012; ISA/EP, with Great Britain Search Report for Priority application GB11006787.3, dated Aug. 11, 2011.
(Continued)

*Primary Examiner* — Bumsuk Won
*Assistant Examiner* — Tamara Y Washington
(74) *Attorney, Agent, or Firm* — Harness, Dickey & Pierce, P.L.C.

(57) ABSTRACT

Methods and apparatus for optimising, improving or maximising the efficiency of an acousto-optic lens (AOL) system are disclosed. Data relating to efficiency is used to select drive frequencies of the acousto-optic devices (AODs) forming the AOL, thereby both increasing the usable field of view and reducing a prior art patternation problem. Preferably according to the invention, drive frequencies are selected that maximise efficiency of transmission through the AOL. When scanning, the centre of each scan is optimised to be of maximum efficiency.

12 Claims, 10 Drawing Sheets

(51) Int. Cl.
*G02F 1/33* (2006.01)
*G02B 21/00* (2006.01)
*G02B 21/16* (2006.01)
*G01N 21/64* (2006.01)

(56) References Cited

U.S. PATENT DOCUMENTS

| | | | |
|---|---|---|---|
| 4,371,964 | A | 2/1983 | Podmaniczky et al. |
| 4,435,041 | A | 3/1984 | Torok et al. |
| 4,443,066 | A | 4/1984 | Freyre |
| 4,514,056 | A | 4/1985 | Azgapetian |
| H884 | H | 2/1991 | Gottlieb |
| 5,034,613 | A | 7/1991 | Denk et al. |
| 5,197,074 | A | 3/1993 | Emmons, Jr. et al. |
| 5,296,700 | A | 3/1994 | Kumagai |
| 5,365,239 | A | 11/1994 | Stilwell, Jr. |
| 5,491,587 | A | 2/1996 | Iwaki et al. |
| 5,644,437 | A | 7/1997 | Maruyama et al. |
| 5,646,411 | A | 7/1997 | Kain |
| 5,680,252 | A | 10/1997 | Sitter, Jr. et al. |
| 5,825,497 | A | 10/1998 | Kim |
| 5,946,141 | A | 8/1999 | Harrigan |
| 6,166,385 | A | 12/2000 | Webb et al. |
| 6,285,507 | B1 | 9/2001 | Sakamoto |
| 6,307,665 | B1 | 10/2001 | Kim et al. |
| 6,344,653 | B1 | 2/2002 | Webb et al. |
| 6,473,233 | B1 | 10/2002 | Iizuka |
| 6,587,255 | B2 | 7/2003 | Davidson et al. |
| 6,906,824 | B1 | 6/2005 | Kamikubo et al. |
| 8,294,977 | B2 * | 10/2012 | Kirkby et al. ............... 359/310 |
| 2002/0030890 | A1 | 3/2002 | Kato et al. |
| 2002/0057642 | A1 | 5/2002 | Kim et al. |
| 2002/0136524 | A1 | 9/2002 | Agha Riza |
| 2002/0141035 | A1* | 10/2002 | Davidson et al. ............ 359/285 |
| 2002/0149769 | A1 | 10/2002 | Roorda et al. |
| 2002/0149856 | A1 | 10/2002 | Chen et al. |
| 2003/0156323 | A1 | 8/2003 | Overbeck |
| 2005/0045814 | A1 | 3/2005 | Shimomura et al. |
| 2005/0061981 | A1 | 3/2005 | Allen et al. |
| 2005/0117221 | A1 | 6/2005 | Ogawa |
| 2005/0226557 | A1 | 10/2005 | Trutna et al. |
| 2005/0259306 | A1 | 11/2005 | Broome et al. |
| 2005/0263690 | A1 | 12/2005 | Araya et al. |
| 2005/0279807 | A1 | 12/2005 | Johnson |
| 2006/0056062 | A1 | 3/2006 | Cheng |
| 2006/0071143 | A1 | 4/2006 | Saggau et al. |
| 2006/0087737 | A1 | 4/2006 | Choi et al. |
| 2008/0180782 | A1 | 7/2008 | Kump et al. |

FOREIGN PATENT DOCUMENTS

| | | |
|---|---|---|
| EP | 0899603 | 3/1999 |
| EP | 1043615 | 10/2000 |
| EP | 1184855 | 3/2002 |
| EP | 1467235 | 10/2004 |
| EP | 1587185 | 10/2005 |
| EP | 1596283 | 11/2005 |
| EP | 1862838 | 12/2007 |
| EP | 1870762 | 12/2007 |
| FR | 2708355 | 2/1995 |
| GB | 2119109 | 11/1983 |
| GB | 2368656 | 5/2002 |
| JP | S63194236 A | 8/1988 |
| JP | 03004216 A | 1/1991 |
| JP | 05034735 A | 2/1993 |
| JP | 06082851 A | 3/1994 |
| JP | 07335526 A | 12/1995 |
| JP | 08328050 A | 12/1996 |
| JP | 11218682 A | 8/1999 |
| JP | 2004535596 A | 11/2004 |
| WO | 02057811 | 7/2002 |
| WO | 03046613 | 6/2003 |
| WO | 2006042130 | 4/2006 |
| WO | 2008032061 A2 | 3/2008 |
| WO | 2010076579 A1 | 7/2010 |

OTHER PUBLICATIONS

BR Brown et al. "Acoustic Light Deflector Chromatic Variation Compensation." Feb. 1, 1971.

European Search Report regarding Application No. 13170153.4-1903, dated Jul. 16, 2013.

European Search Report regarding Application No. 13170151.8-1903, dated Jul. 15, 2013.

European Search Report regarding Application No. 13170156.7-1903, dated Jul. 11, 2013.

Kirkby, P.A., et al. "A compact acousto-optic lens for 2D and 3D femtosecond based 2-photon microscopy." Optics Express Optical Society of America USA, vol. 18, No. 13, Jun. 11, 2010, pp. 13721-13745, XP000002654264, ISSN: 1094-4087.

International Search Report regarding PCT/GB2001/000608, mailed Aug. 16, 2011; ISA/EP with Great Britain Search Report for priority application GB1006679.3, dated Jul. 28, 2010.

Great Britain Search Report for priority Application No. GB0800333.7 dated May 8, 2008.

Great Britain Search Report for priority Application No. GB0617945.1 dated Aug. 15, 2007.

International Search Report regarding PCT/GB2011/000608 mailed Aug. 16, 2011.

Japanese Office Action dated Jan. 14, 2014 with translation provided by J A Kemp.

Kirkby, P.A., et al., "A compact acousto-optic lens for 2D and 3D femtosecond based 2-photon microscopy", Optics Express Optical Society of America USA, vol. 18, No. 13, Jun. 11, 2010, pp. 13721-13745, XP000002654264, ISSN: 1094-4087.

Kaplan, A., et al., "Acousto-Optic Lens with Very Fast Focus Scanning", Optics Letters, OSA, Optical Society of America, Washington, DC, US, vol. 26, No. 14, Jul. 15, 2001, pp. 1078-1080, XO001103640, ISSN: 0146-1080.

Reddy, G. D. et al: "Fast three-dimensional laser scanning scheme using acousto-optical deflectors," Journal of Biomedical Optics SPIE USA, vol. 1-, No. 6, Nov. 2005, pp. 64038-1, XP002471695, ISSN: 1083-3668.

Iyer, V et al: "Compensation of spatial and temporal dispersion for acousto-optic multiphoton laser-scanning microscopy," Journal of Biomedical Optics SPIE USA, vol. 8, No. 3, Jul. 2003, pp. 460-471, XP002471781, ISSN: 1083-3668.

Bewersdorf, J., Pick, R., and hell, S.W. (1998) Multifocal Multiphoton Microscopy. Optics Letters 23, 655-657.

Botcherby, E.J., Juskaitis, R., Booth, M.J., and Wilson, T. (2007). Aberration-Free Optical Refocusing in High Numerical Aperture Microscopy. Optics Letters 32 (14), 2007-2009.

Carter, A.G., and Sabatini, B.L. (2004). State-Dependent Calcium Signaling in Dendritic Spines of Striatal Medium Spiny Neurons. Neuron 44, 483-493.

Chaigneau, E., Oheim, M., Audinat, E., and Charpak, S. (2003). Two-Photon Imaging of Capillary Blood Flow in Olfactory Bulb Glomeruli. Proc Natl Acad Sci U S A 100, 13081-13086.

Cossart, R., Aronov, D., and Yuste, R. (2003). Attractor dynamics of network UP states in the neocortex. Nature 423, 283-288.

Denk, W., Piston, D.W., and Webb, W.W. (1995). Two photon molecular excitation in laser-scanning microscopy. In Handbook of Confocal Microscopy, J.B. Pawley, ed. (Plenum), pp. 445-458.

Denk, W., Strickler, J.H., Webb, W. W. (1990). Two-Photon Laser Scanning Fluorescence Microscopy. Science, New Series, 248 (4951), 73-76.

Denk, W., and Svoboda, K. (1997). Photon upmanship: why multiphoton imaging is more than a gimmick. Neuron 18, 351-357.

DiGregorio, D.A. Nielsen, T.A., and Silver, R.A. (2004). Investigation of Synaptic Ampa Receptors with Glutamate Uncaging using a Diffraction-Limited UV Spot. Online Abstact Society for Neuroscience Program No. 404.4.

(56) References Cited

OTHER PUBLICATIONS

DiGregorio, D.A., Rothman, J.S., Nielsen, T.A., and Silver, R.A., (2007). Desensitization Properties of AMPA Receptors at the Cerebellar Mossy Fiber-Granule Cell Synapse Journal of neuroscience, 27(31), 8344-8357.

Fan, G.Y., Fujisaki, H., Miyawaki, A., Tsay, R.K., Tsien, R.Y., and Ellisman, M.H. (1990). Video-rate scanning two-photon excitation fluorescence microscopy and ratio imaging with cameleons. Biophys J 76, 2412-2420.

Gobel, W., Kampa, B.M. and Helmchen, F. (2007). Imaging cellular network dynamics in three dimensions using fast 3D laser scanning. Nature Methods 4 (1), 73-79.

Hopt, A., and Neher, E. (2001). Highly nonlinear photodamage in two-photon fluorescence microscopy. Biophys J 80, 2029-2036.

Iyer V, Hoogland TM, Saggau P (2006) Fast functional imaging of single neurons using random-access multiphoton (RAMP) microscopy. Journal of Neurophysiology 95:535-545.

Kiskin, N. I., Chillingworth, R., McCray, J.A., Piston, D., and Ogden, D. (2002). The efficiency of two-photon photolysis of a "caged" fluorophore, o-1-(2-nitrophenyl) ethylpyranine, in relation to photodamage of synaptic terminals. Eur Biophys J 30, 588-604.

Kiskin, N. I. and Ogden, D. (2002. Two-photon excitation and photolysis by pulsed laser illumination modelled by spatially non-uniform reactions with simultaneous diffusion. Eur Biophys J 30, 571-587.

Koester, H.J., Baur, D., Uhl, R., and Hell, S.W. (1999). Ca2+fluorescence imaging with pico-and femtosecond two-photon excitation: signal and photodamage. Biophys J 77, 2226-2236.

Lechleiter, J.D., Lin, D.T., and Sieneart, I. (2002). Multi-photon laser scanning microscopy using an acoustic optical deflector. Biophys J 83, 2292-2299.

Margrie, T.W., Meyer, A.H., Caputi, A., Monyer, H., Hasan, M.T., Schaefer, A.T., Denk, W., and Brecht, M. (2003). Targeted whole-cell recordings in the mammalian brain in vivo. Neuron 39, 911-918.

Matsuzaki, M. Ellis-Davies, G.C., Nemoto, T., Miyashita, Y., Iino, M., and Kasai, H. (2001). Dendritic Spine Geometry is Critical for AMPA receptor expression in Hippocampal CA1 pyramidal neurons. Nat Neurosci 4, 1086-1092.

Ngoi, B.K.A., Venkatakrishnan, K., Tan, B., Stanley, P., and Lim, L.E.N. (2001). Angular dispersion compensation for acousto-optic devices used for ultrashort-pulsed laser micromachining. Optics Express 9, 200-206.

Oheim, M., Beaurepaire, E., Chaigneau, E., Mertz, J., and Charpak, S. (2001). Two-photon microscopy in brain tissue; parameters influencing the imaging depth. J. Neurosci Methods 111, 29-37.

Reddy D & Saggau P (2007) Fast Trhee-Dimensional Random Access Multi-Photon Microscopy for Functional Recording of Neuronal Activity, Proceedings of SPIE, vol. 6630 Confocal, Multiphoton, and nonlinear Microscopic Imaging III, Tony Wilson, Ammasi Periasamy, Editors, 66301A.

Reddy D & Saggau P (2007) Development of a random access multiphoton microscope for fast three-dimensional functional recording of neuronal activity, Proceedings of SPIE vol. 6443 Three-Dimensional and Multidimensional Microscopy: Image Acquisition and Processing XIV, Jose-Angel Conchello, Carol J. Cogswell, Tony Wilson, Editors, 64430U.

Roorda, R.D., Hohl, T.M., Toledo-Crow, R., and Miesenbock, G. (2004). Video-rate nonlinear microscopy of neuronal membrane dynamics with genetically encoded probes. J. Neurophysiol 92, 609-621.

Salome R, Kremer Y, Dieudonne S, Leger JF, Krichevsky O, Wyart C, Chatenay D, Bourdieu L. (2006) Ultrafast Random-Access Scanning in Two-Photon Microscopy Using Acousto-Optic Defelctors. Neurosci Methods. Jun. 30; 154 (1-2): 161-174.

Smith, M.A., Ellis-Davies, G.C., and Magee, J.C. (2003). Mechanism of the distance-dependent scaling of Schafer collateral synapses in rat CA1 pyramidal neurons. J Physiol 548, 245-258.

Stosiek, C., Garaschuk, O., Holthoff, K., and Konnerth, A. (2003). In vivo two-photon calcium imaging of neuronal networks. Proc Natl Acad Sci U S A 100, 7319-7324.

Young E H, Huey C H & Harrison L (1990) Optically Rotated long Time Aperture TeO2 Bragg cell. Proceedings of SPIE vol. 1296 Advances in Optical information processing IV, 304-315.

Zipfel, W.R., Williams, R.M., and Webb, W.W. (2003). Nonlinear magic: Multiphoton Microscopy in the Biosciences. Nat Biotechnol 21, 1369-1377.

Office Action regarding Japanese Patent Application No. 2009-527885 mailed Jun. 5, 2012. Translation provided by J.A. Kemp.

Office Action regarding U.S. Appl. No. 12/440,809 mailed Mar. 22, 2012.

International Search Report regarding International Application No. PCT/GB2009/000061 dated Apr. 20, 2009.

International Search Report regarding International Application No. PCT/GB2007/003455 dated Aug. 11, 2008.

International Search Report for PCT/GB/2001/000608, mailed Aug. 11, 2011; ISA/EP with Great Britain Search Report for priority application GB1006679.3, dated Jul. 28, 2010.

International Search Report for PCT/GB2012/050824, mailed Jun. 22, 2012; ISA/EP, with Great Britain Search Report for priority application GV11006787.3, dated Aug. 11, 2011.

* cited by examiner

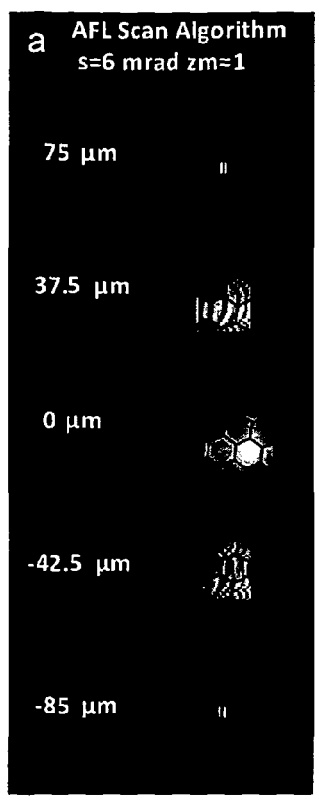 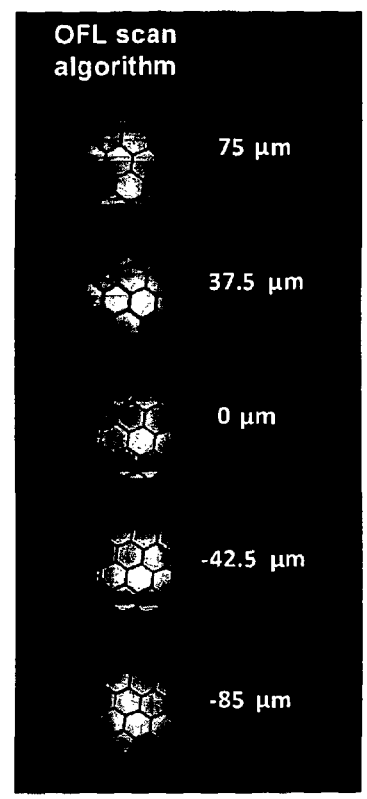
Fig. 19                               Fig. 20

METHODS AND APPARATUS FOR CONTROLING DRIVE FREQUENCIES OF ACOUSTO-OPTIC DEFLECTORS

CROSS-REFERENCE TO RELATED APPLICATIONS

This application is a 371 U.S. National Stage of International Application No. PCT/GB2011/000608, filed on Apr. 20, 2011. This application claims priority to British Patent Application No. 1006679.3, filed on Apr. 21, 2010. The contents of the above applications are incorporated herein by reference in their entirety.

The present invention relates to apparatus and methods involving the manipulation of a beam of electromagnetic radiation, such as a laser beam. More particularly, the invention relates to apparatus and methods for configuring an acousto-optic lens to cause a beam to be deflected in a desired way. In preferred embodiments, the beam is made to image a target space, such as by selectively focussing the beam in the target space, which may be a point, 1D line, 2D plane or a 3D volume.

The ability to steer and focus electromagnetic radiation, such as a laser beam, rapidly in three-dimensions is very attractive for several applications in biology, microfabrication and data storage.

Laser scanning confocal imaging is an important and widely used tool in biology because it allows high contrast visualization of subcellular structures and monitoring of physiological processes with fluorescence indicators within living tissue by excluding contaminating out-of focus light. Conventional confocal methods work best at relatively shallow depths where light penetration is good and scattering is minimal. Usually, conventional confocal imaging cannot be used to image biological activity deep (>100 μm) within the living tissue. However, a type of laser scanning confocal microscopy has been developed that relies on non-linear multiphoton excitation to generate second or higher order harmonic light at shorter wavelength or selectively activate fluorophores where the light intensity exceeds the multiphoton threshold at the centre of the focal volume. Such fluorescent light is emitted in all directions by these fluorophores and is typically picked up by a high numerical aperture lens system and photomultipliers placed anywhere convenient whereas harmonic light is more directional and may need the high aperture lens placed appropriately. As the focal spot is scanned through the tissue the light intensity emitted by the harmonic process or fluorophores varies according to non linearity of the biological tissue or the intensity of staining by the fluorescence indicators in that part of the tissue, respectively. Combining the photomultiplier signal with the known position of the 2-photon focal volume enables a point, 1D, 2D or 3D image of the fluorescence intensity within the tissue to be reconstructed. This technique, known as two-photon microscopy, allows imaging at much greater depth than confocal microscopy because of the longer excitation wavelengths used for multiphoton excitation (wavelengths of 700-1000 nm), which scatter less than those used in conventional confocal imaging, and because confocality arises intrinsically from the excitation volume allowing all emitted photons to be used to construct the image. These properties together with the low levels of photodamage achievable have made 2-photon imaging an extremely powerful method for examining physiological processes at the cellular and subcellular levels both in vitro and in vivo.

Two-photon imaging has been particularly popular in neuroscience, as it has allowed the dynamic properties of neuronal network activity to be imaged in intact brain tissue using calcium indicators. The spatial resolution of 2-photon microscopy is well suited to this task even allowing the small synaptic connections between neurons to be resolved. Multiphoton excitation has also begun to be used to photolyse "caged compounds" that release neurotransmitters, allowing synaptic inputs onto a cell to be mimicked. This technique is potentially very important for understanding synaptic integration and thus determining how individual neurons carry out low-level computations.

Other applications of light microscopy include imaging morphological structures and controlling neuronal activity with genetically encoded light activated proteins.

Many physiological processes of interest occur rapidly, on the 1-100 ms timescale, in small cellular structures within tissue that absorbs and scatters light. The deep tissue penetration and submicrometer resolution that 2-photon microscopy provides has made this approach popular for studying such biological phenomena. However, current 2-photon microscopes, which use galvanometer mirrors to steer the laser beam, and build up an image, are too slow to monitor many fast spatially distributed processes, which occur on the 1-100 ms time scale, since they typically take 100 ms to form an image. Moreover, most microscopes developed to date are optimized for imaging a single X-Y plane. Focussing in the Z direction is typically achieved by moving the apparatus relative to the sample (for example by moving the objective lens closer to or further away from the sample).

The use of galvanometer mirrors has an inherent disadvantage in that the mirrors necessarily have a mass and the speed at which the mirror can be moved from one position to another is limited by inertia. In practical terms, this means that it takes of the order of 200-300 μs to move a mirror from one selected position to another selected position. In turn, this limits the number of spots upon which a laser beam can be focussed during a given time frame. These constraints are particularly limiting for studying brain function, since information is encoded and transmitted as brief electrical impulses (~1 ms) in groups of neurons distributed in a 3D space.

The temporal resolution of the present state of the art galvanometer-based imaging systems is one or two orders of magnitude too slow to accurately image signalling in a network of neurons in 3D space. In such neurons, the elementary signal event (action potentials) occurs on the millisecond time scale. Moreover, the signals are spatially distributed in three-dimensions as they flow through the neural networks and building a 3-D stack of images using galvanometer-based technology takes minutes. Furthermore, galvanometers are too slow for monitoring calcium concentration in networks of neurons using calcium sensitive dyes even when the monitoring is restricted to pointing rapidly from one region of interest to another rather than scanning the full volume. Such imaging can monitor action potentials in neurons because intracellular calcium concentration depends on cell membrane potential. The excitation beam needs to be moved to many (for example 30) separate neuron sites within a millisecond in order to monitor signals distributed over the network. For example, assuming that it takes 300 μs to move from one spot to another using a galvanometer mirror and assuming a dwell time at each spot of 5 μs, it would take 9.15 ms to image 30 sites. This is approximately 10 times too slow for current needs.

Several strategies have been employed to improve the temporal resolution when imaging. These include using resonance scanners which speed scanning and image acquisition but reduce the dwell time, thereby limiting their utility except for the brightest fluorescent preparations.

One approach suggested in the prior art to address some of these disadvantages is to use rapid acousto-optic deflectors (AODs) instead of galvanometers to steer the two-photon laser beam. AODs provide a fast, mass-less scanning solution that is not limited by inertia. The advantage of using AODs is that they allow the beam of radiation to be moved much more rapidly from point-to-point than in a galvanometer-based system (compare a movement time of 5-25 μs with AODs to 200-400 μs with galvanometers). This has several potential advantages. Firstly, images can be scanned rapidly. Secondly, multiple point measurements can be made with long dwell times at very high temporal resolution (e.g. using an AOD system with a 15 μs movement time, 33 points can be simultaneously sampled at a 1 KHz sample rate with a 15 μs dwell time or, in other words, 33 different points can be monitored 1000 times per second) This in known as random access multiphoton (RAMP) microscopy. The use of AODs therefore allows much more of the time to be devoted to actually collecting photons from the regions of interest rather than being taken up in moving the beam between sites.

As well as deflecting the beam in the X-Y plane, the use of two AODs per axis can, in principle, also be used to focus the laser beam in the Z-dimension. For example, Kaplan et al describe in "*Acousto-Optic Lens with Very Fast Focus Scanning*" Optics Letters, Vol. 26, No. 14, Jul. 15, 2001, pp 1078-1080, the use of two or four AODs to focus a laser beam in the X and Z plane or anywhere in an X-Y-Z volume. To achieve focussing in a 3D volume, two AODs for focussing in the X-Z plane are followed by two AODs for focussing in the Y-Z plane. These ideas are further developed in WO 2008/032061, where a compact configuration of AODs is first disclosed and the practical equations for driving these AODs are first given.

Several laboratories have developed scanners with two AODs to make fast 2-photon fluorescent measurements from neurons and for single photon photolysis in 2D. However, the disadvantage of this approach is that forming an image is complicated by chromatic and temporal dispersion and the fact that as the speed of scanning is increased the AOD introduces a focussing effect. The resulting astigmatism of the illumination point spread function (iPSF) can be corrected with lenses but only for a single scan speed, so most microscopes using two AODs use point measurements to build up an image, which is slow and can take several seconds per image. Moreover, monitoring signals in 3D with 2 AODs is limited because the focus is inexorably linked to scan speed and dwell time.

There have been several recent advances in high speed 3D imaging. Sampling many locations (~100 neurons) within a 250 μm cube of cortex at 10 Hz has been achieved by combining fast piezoelectic control of the objective with sophisticated galvanometer based scanning[see W. Gobel, B. M. Kampa, and F. Helmchen, "*Imaging cellular network dynamics in three dimensions using fast 3D laser scanning*," Nat Methods 4, 73-79 (2007)]. Faster continuous focussing has been demonstrated using a piston mirror, and an ingenious dual objective system that corrects for spherical aberrations [see E. J. Botcherby, R. Juskaitis, M. J. Booth, and T. Wilson, "*Aberration free optical refocusing in high numerical aperture microscopy*," Opt Lett 32, 2007-2009 (2007)]. The focusing properties of AODs have also been utilized for high speed focusing.

Kaplan et al., first demonstrated that 2 AODs with counter propagating chirped acoustic waves could be used to produce a high speed (400 kHz) cylindrical lens. They also proposed that four AODs could potentially be used to generate a spherical lens. These ideas have been developed further and a proof of principle 3D 2 photon microscope recently has been built that can focus rapidly and perform RAMP measurements [see G. Reddy, K. Kelleher, R. Fink, and P. Saggau, "*Three-dimensional random access multiphoton microscopy for functional imaging of neuronal activity*," Nat Neurosci 11, 713-720 (2008)]. However, a limitation of this system, which is based on 4 conventional AODs, was that light transmission efficiency drops off rapidly if the light is focused more than ±25 μm from the natural focal plane of the objective. Fast pointing was demonstrated within a 3D octahedral shaped field of view, by measuring calcium transients in neuronal processes, but the temporal dispersion of the laser pulses to the picosecond range, resulted poor 2-photon excitation efficiency. Moreover, imaging formation was slow (seconds) because it was limited to point measurements. This is problematic because RAMP measurements require a stack of high resolution images of the volume to be studied so that ROIs can be accurately selected. These and other technical difficulties have prevented AODs from being widely accepted as suitable deflectors for 2-photon microscopy up to now.

Many of these technical difficulties have been addressed by using a compact spherical acousto-optic lens (AOL) that can be used to scan and focus a femtosecond laser beam at high speed, as disclosed in WO2008/032061. At the core of this AOL are four acousto-optic crystals with properties optimized for their function. By incorporating the AOL in a conventional 2-photon microscope a high speed 3D 2-photon microscope can be created that can image rapidly in raster-scan mode and perform RAMP measurements in 3D at 30 kHz. The improvements in performance resulting from several of the innovations in this filing were reported in Paul A. Kirkby, K. M. Naga Srinivas Nadella, and R. Angus Silver, "*A compact acousto-optic lens for 2D and 3D femtosecond based 2-photon microscopy*," Opt. Express 18, 13720-13744 (2010).

A dynamic cylindrical lens formed of two AODs is illustrated in FIG. 8 of WO2008/032061. The acoustic transducer on each AOD crystal produces an ultrasonic sound wave that propagates across the optical aperture of the crystal. The sound wave induces changes in refractive index of the crystal, which diffracts the incoming laser beam at an angle determined by the frequency of the sound wave. By changing the sound frequency with time (chirping) the optical wave front can be curved bringing it to a line focus in the X-Z plane. A stationary focus requires two counter propagating AODs to cancel movement produced by the curtain of sound as it propagates across the crystal. Two AODs can thus be used to form a stationary cylindrical lens.

As shown in FIGS. 7 and 8 of WO2008/032061, increasing the negative chirp rate moves the line focus up (increasing Z), whilst adjusting the difference between the ramp centre frequencies adjusts the X position. Changing to a positive chirp rate produces a diverging optical wave front with a virtual focus above the AODs. A second pair of counter propagating AODs orthogonal to the first can be used to focus in the Y-Z plane (see FIG. 10 of WO 2008/032061). These AODs are preferably interleaved with the first AODS and are accompanied by half-wave plates and polarisers, as disclosed in WO 2008/032061. The four AODs can shape the optical wave front to give a spherically diverging or converging beam. This can be used to focus to a point above and below the natural focal plane of a subsequent fixed lens system.

The device of WO 2008/032061, although producing very good results, suffers from two disadvantages. Firstly, the field of view, that is to say the total volume of space that is addressable using the system, is of an octahedral shape, as shown in FIG. 2 of the attached drawings. This shape can be described as two square-based pyramids joined together base-to-base.

When a typical coordinate system is used, such that a depth of Z=0 is equivalent to the focus achieved when unchirped frequencies are supplied to the AODs (as shown in FIG. 7b of WO 2008/032061), an X-Y plane of the largest size may be addressed at depths of Z=0. This can be further understood by referring to FIGS. 7 and 8 of WO 2008/032061. For the plane at Z=0, the slope of the drive frequency ramps is set to zero. Accordingly, there is no chirp on the drive signals and the beam of electromagnetic radiation can be pointed to any position in the X-Y plane, with the only limitation being the maximum possible deflection angle allowed by the AODs. For depths where Z≠0, a frequency ramp (chirped signal) must be applied to the drive signals. The larger the depth from the Z=0 plane, the steeper the ramp that is required. The steeper the ramp that is applied, the sooner one reaches either the minimum ($f_{min}$) or maximum ($f_{max}$) allowed frequencies for driving the AODs.

In order to obtain the largest usable signal, it is necessary for the AOD to be full of a sound wave with one ramp rate. This takes one AOD fill time, typically 24 us depending on AOD aperture. In addition one needs a certain minimum dwell time at the chosen location to collect photons, say another 4 μs. Accordingly, there will be one value of Z where frequency ramping from the minimum frequency $f_{min}$ to the maximum frequency $f_{max}$ takes precisely 28 μs. For larger values of Z (and therefore larger required ramp gradients), it will take a shorter time to move from $f_{min}$ to $f_{max}$ and so it is not in these cases possible to provide the necessary ramp to the drive signals for the dwell time needed to image a point a space. As a result, the octahedral field of view shown in FIG. 2 is obtained, with the top and bottom apexes of the octahedron representing the values of Z where the ramp chirp is such that a single point along the Z-axis may be imaged before the AOD frequency limits are reached. The Z=0 plane represents the maximum extent of X and Y deflection possible, because no chirping is necessary and so the full range of possible frequencies can be used to deflect the beam in the X or Y plane. At points between the Z=0 plane and the apexes, a limited amount of X, Y and Z deflection is possible.

This octahedral field of view is undesirable because for many applications it would be more useful to have a less limited field of view. In particular, it would be useful to have a field of view that is more nearly cuboid, such that the amount of X and Y deflection is not so limited as a function of the amount of Z deflection. Accordingly, a first problem lies in the limited octahedral field of view achievable with the device of Kaplan and WO 2008/032061.

Image results obtained using the device of WO 2008/032061 are shown in FIG. 3 of the attached drawings. This Figure shows the complete field of view beneath an NA=0.47, 20× objective for the normalised Z range from −0.8 to +0.8 in steps of 0.2 and a semiscan angle s=4.3. The image is formed by 2-photon imaging with the beam scanning across a plastic luminescent slide (Chroma Technologies), above which has been placed a 42 μm pitch hexagonal electron microscope (EM) grid made of copper. This forms the hexagonal shadow pattern on the luminous background and allows the field of view to be measured accurately. For each 2D image plane the stage was moved mechanically to bring the image into focus at the Z focal plane defined by the AOD focal setting (Z axis). Nine images in total are shown, taken at different values of Z. The octahedral imaging capability is readily noticeable from FIG. 3.

Also noticeable is a patternation effect in many of the resulting images. This is particularly noticeable for the images just above and below the Z=0 plane. These patternation effects result from the fact that, to build up a complete image in planes where Z≠0, it is necessary to use a series of "mini-scans". These are described in WO 2008/032061 with reference to FIG. 46 of that document. In short, it is necessary to reset the AOD drive frequencies once the frequency limits have been reached and, because the efficiency of transmission is somewhat dependent on the frequencies applied to the AODs, different brightnesses are seen in the final image. For drive frequencies that lead to a high transmission efficiency, the voxel is brighter than for drive frequencies that lead to low transmission efficiency.

In theory, the patternation effect could be reduced by further limiting the range of frequencies that are used to drive the AODs (i.e. $f_{min}$ could be increased and $f_{max}$ could be reduced). There would then be a smaller variation of transmission efficiency for each mini-scan, and the brightness variations would be reduced. However, this itself would lead to a reduced field of view, effectively serving to make the octahedron of FIG. 2 even smaller. As such, this attempt to solve the patternation problem would lead to a reduction in the field of view, thereby amplifying the field of view problem discussed above.

It would be highly desirable to devise a method and apparatus that could address both of the above problems at the same time, without having to compromise on either the field of view or the patternation reduction.

The present invention indeed addresses both of the above problems simultaneously and provides a method and apparatus that can be used to both increase the field of view, especially where Z≠0 and reduce patternation effects. Accordingly, the present invention represents a very significant step forward in the art.

In one aspect, the invention comprises a method of configuring an acousto-optic lens for manipulating a beam of electromagnetic radiation so as to be deflected and focussed toward a desired location in space, said acousto-optic lens comprising at least a first acousto-optic deflector driven by a first drive frequency and a second acousto-optic deflector driven by a second drive frequency, said method comprising: for each of a plurality of possible locations in space, separately storing data related to a preferred frequency pair, wherein a preferred frequency pair for an associated possible location in space consists of a first preferred drive frequency for said first acousto-optic deflector and a second preferred drive frequency for said second acousto-optic deflector, said preferred frequency pair being such that if said first and second preferred drive frequencies of said pair were applied at the same time to said respective first and second acousto-optic deflectors, said beam of electromagnetic radiation would be deflected toward said associated possible location in space; consulting said data to determine a preferred frequency pair based on said desired location in space; determining first and second drive frequencies as a result of said consulting step.

This method allows the areas of high efficiency operation to be recalled quickly and easily, and thereby allows the AOL to be used with higher efficiency than in the prior art, reducing patternation and increasing the field of view.

In one method, said stored data comprises frequency modification data and consulting said data comprises: determining a pair of reference frequencies for said desired location in space, said pair of reference frequencies being such that if the reference frequencies of said pair were applied to said respective first and second acousto-optic deflectors, said beam of electromagnetic radiation would be deflected toward said desired location in space; consulting the stored data to obtain frequency modification data; and modifying said pair of reference frequencies according to said frequency modification data to obtain said preferred frequency pair.

The modifying could comprise adding or subtracting a common mode component to/from said reference frequency pair.

Determining the first and second drive frequencies may comprise setting said first and second drive frequencies to be respectively equal to said first and second preferred drive frequencies of the preferred frequency pair.

This method is preferably executed with a look-up table. It allows a common mode frequency offset to be established that approximates the optimum for the desired location. This places the operation in the area of higher efficiency.

In another method, consulting said data comprises identifying the data stored for the possible location that is closest to said desired location and determining that that data relates to the preferred frequency pair for said desired location in space.

Preferably, determining the first and second drive frequencies comprises modifying said preferred frequency pair so as to obtain a drive frequency pair such that if the drive frequencies of said drive frequency pair were applied to said respective first and second acousto-optic deflectors, said beam of electromagnetic radiation would be deflected toward said desired location in space.

The modifying can comprise adding or subtracting a differential mode component to/from said preferred frequency pair.

This method is also preferably executed with a look-up table. Instead of storing common mode offsets, preferred frequency pairs can be stored directly. It allows a preferred frequency pair to be established that is optimum for a position that approximates the desired location. The preferred pair can be modified to get to the exact correct position. This again places the operation in the area of higher efficiency.

Other methods are available that can be used according to the invention. For example, raw efficiency data can be stored and consulted in real time.

In another aspect, the invention comprises a method of configuring an acousto-optic lens for manipulating a beam of electromagnetic radiation so as to scan from a start location to an end location along a mini-scan path, said acousto-optic lens comprising at least a first acousto-optic deflector driven by a first drive frequency and a second acousto-optic deflector driven by a second drive frequency, said method comprising for each of a plurality of possible locations in space, separately storing data related to a preferred frequency pair, wherein a preferred frequency pair for an associated possible location in space consists of a first preferred drive frequency for said first acousto-optic deflector and a second preferred drive frequency for said second acousto-optic deflector, said preferred frequency pair being such that if said first and second preferred drive frequencies of said pair were applied at the same time to said respective first and second acousto-optic deflectors, said beam of electromagnetic radiation would be deflected toward said associated possible location in space; consulting said data to determine a preferred frequency pair based on said mini-scan path; determining first and second drive frequencies as a result of said consulting step.

This method allows a scan to be carried out using knowledge of the high efficiency areas of operation. As such patternation is reduced and the field of view is increased.

Preferably, the consulting step comprises: determining a reference location lying along said mini-scan path; and determining a preferred drive frequency pair in accordance with the determined reference location.

Preferably, the reference location lies at the midpoint of said mini-scan path.

In one method, the stored data comprises frequency modification data and wherein consulting said data comprises: determining a pair of reference frequencies for said reference location in space, said pair of reference frequencies being such that if the reference frequencies of said pair were applied to said respective first and second acousto-optic deflectors, said beam of electromagnetic radiation would be deflected toward said reference location in space; consulting the stored data to obtain frequency modification data; and modifying said pair of reference frequencies according to said frequency modification data to obtain said preferred frequency pair.

The modifying can comprise adding or subtracting a common mode component to/from said reference frequency pair.

Determining the first and second drive frequencies could comprise setting said first and second drive frequencies to be respectively equal to said first and second preferred drive frequencies of the preferred frequency pair.

In another method, consulting said data comprises identifying the data stored for the possible location that is closest to said reference location and determining that that data relates to the preferred frequency pair for said reference location.

Determining the first and second drive frequencies can comprise modifying said preferred frequency pair so as to obtain a drive frequency pair such that if the drive frequencies of said drive frequency pair were applied to said respective first and second acousto-optic deflectors, said beam of electromagnetic radiation would be deflected toward said reference location.

The modifying could comprise adding or subtracting a differential mode component to/from said preferred frequency pair.

In a preferable aspect, said data related to a preferred frequency pair is data allowing determination of the frequency pair that will cause said beam of electromagnetic radiation to be transmitted through said acousto-optic lens toward said associated possible location in space at the highest efficiency.

In a preferred aspect, consulting said data to determine the preferred frequency pair comprises performing a calculation on the stored data to obtain the preferred frequency pair.

Typically, there is separately stored data related to a preferred frequency pair for each of at least nine locations in space.

In any of the above methods, said acousto-optic lens can additionally comprise a third acousto-optic deflector driven by a third drive frequency and a fourth acousto-optic deflector driven by a fourth drive frequency, said method additionally comprising: for each of said plurality of possible locations in space, storing data related to a second preferred frequency pair, wherein a second preferred frequency pair for an associated possible location in space consists of a third preferred drive frequency for said third acousto-optic deflector and a fourth preferred drive frequency for said fourth acousto-optic deflector, said second preferred frequency pair being such that if said third and fourth preferred drive frequencies of said second pair were applied at the same time to said respective third and fourth acousto-optic deflectors, said beam of electromagnetic radiation would be deflected toward said associated possible location in space; consulting said data to determine a second preferred frequency pair based on said desired or reference location; determining third and fourth drive frequencies as a result of said consulting step.

The use of third and fourth AODs in addition to the first and second AODs allows a spherical lens to be provided so that the beam may be deflected in both X and Y directions, as well as focussed in the Z direction (due to the use of two AODs per coordinate direction).

In a further aspect, the invention includes a method of deflecting a beam of electromagnetic radiation, said method comprising: determining first and second drive frequencies according to any of the methods described above; applying said first drive frequency to said first acousto-optic deflector; simultaneously applying said second drive frequency to said second acousto-optic deflector; and simultaneously supplying said beam of electromagnetic radiation to the input aperture of said first acousto-optic deflector.

The invention also includes apparatus for controlling an acousto-optic lens for manipulating a beam of electromagnetic radiation so as to be deflected and focussed toward a desired location in space, said acousto-optic lens comprising at least a first acousto-optic deflector driven by a first drive frequency and a second acousto-optic deflector driven by a second drive frequency, said apparatus comprising: a memory configured to separately store, for each of a plurality of possible locations in space, data related to a preferred frequency pair, wherein a preferred frequency pair for an associated possible location in space consists of a first preferred drive frequency for said first acousto-optic deflector and a second preferred drive frequency for said second acousto-optic deflector, said preferred frequency pair being such that if said first and second preferred drive frequencies of said pair were applied at the same time to said respective first and second acousto-optic deflectors, said beam of electromagnetic radiation would be deflected toward said associated possible location in space; a controller configured to consult said data to determine a preferred frequency pair based on said desired location in space; said controller being configured to determine first and second drive frequencies as a result of said consulting.

Said memory is preferably configured to store data that comprises frequency modification data and wherein said controller is configured to: determine a pair of reference frequencies for said desired location in space, said pair of reference frequencies being such that if the reference frequencies of said pair were applied to said respective first and second acousto-optic deflectors, said beam of electromagnetic radiation would be deflected toward said desired location in space; consult the stored data to obtain frequency modification data; and modify said pair of reference frequencies according to said frequency modification data to obtain said preferred frequency pair.

Said controller is optionally configured to add or subtract a common mode component to/from said reference frequency pair.

Said controller is optionally configured to set said first and second drive frequencies to be respectively equal to said first and second preferred drive frequencies of the preferred frequency pair.

Said controller is optionally configured to identify the data stored for the possible location that is closest to said desired location and determine that that data relates to the preferred frequency pair for said desired location in space.

Said controller is optionally configured to modify said preferred frequency pair so as to obtain a drive frequency pair such that if the drive frequencies of said drive frequency pair were applied to said respective first and second acousto-optic deflectors, said beam of electromagnetic radiation would be deflected toward said desired location in space.

Said controller is optionally configured to add or subtract a differential mode component to/from said preferred frequency pair.

The invention also includes apparatus for controlling an acousto-optic lens for manipulating a beam of electromagnetic radiation so as to scan from a start location to an end location along a mini-scan path, said acousto-optic lens comprising at least a first acousto-optic deflector driven by a first drive frequency and a second acousto-optic deflector driven by a second drive frequency, said apparatus comprising: a memory configured to separately store, for each of a plurality of possible locations in space, data related to a preferred frequency pair, wherein a preferred frequency pair for an associated possible location in space consists of a first preferred drive frequency for said first acousto-optic deflector and a second preferred drive frequency for said second acousto-optic deflector, said preferred frequency pair being such that if said first and second preferred drive frequencies of said pair were applied at the same time to said respective first and second acousto-optic deflectors, said beam of electromagnetic radiation would be deflected toward said associated possible location in space; a controller configured to consult said data to determine a preferred frequency pair based on said mini-scan path; said controller being configured to determine first and second drive frequencies as a result of said consulting.

In such apparatus, said memory is optionally configured to store data that comprises frequency modification data and wherein said controller is configured to: determine a pair of reference frequencies for said reference location, said pair of reference frequencies being such that if the reference frequencies of said pair were applied to said respective first and second acousto-optic deflectors, said beam of electromagnetic radiation would be deflected toward said reference location; consult the stored data to obtain frequency modification data; and modify said pair of reference frequencies according to said frequency modification data to obtain said preferred frequency pair.

Said controller is optionally configured to add or subtract a common mode component to/from said reference frequency pair.

Said controller is optionally configured to set said first and second drive frequencies to be respectively equal to said first and second preferred drive frequencies of the preferred frequency pair.

Said controller is optionally configured to identify the data stored for the possible location that is closest to said reference location and determine that that data relates to the preferred frequency pair for said reference location.

Said controller is optionally configured to modify said preferred frequency pair so as to obtain a drive frequency pair such that if the drive frequencies of said drive frequency pair were applied to said respective first and second acousto-optic deflectors, said beam of electromagnetic radiation would be deflected toward said reference location.

Said controller is optionally configured to add or subtract a differential mode component to/from said preferred frequency pair.

To provide spherical lensing, said acousto-optic lens can additionally comprise a third acousto-optic deflector driven by a third drive frequency and a fourth acousto-optic deflector driven by a fourth drive frequency; said memory being configured to additionally store for each of said plurality of possible locations in space, data related to a second preferred frequency pair, wherein a second preferred frequency pair for an associated possible location in space consists of a third preferred drive frequency for said third acousto-optic deflector and a fourth preferred drive frequency for said fourth acousto-optic deflector, said second preferred frequency pair being such that if said third and fourth preferred drive frequencies of said second pair were applied at the same time to said respective third and fourth acousto-optic deflectors, said beam of electromagnetic radiation would be deflected toward said associated possible location in space; said controller being configured to consult said data to determine a second preferred frequency pair based on said desired or reference location; said controller being configured to determine third and fourth drive frequencies as a result of said consulting.

The invention also includes in a further aspect a microscope for deflecting a beam of electromagnetic radiation toward a desired location in space, said microscope comprising: an acousto-optic lens comprising at least a first acousto-optic deflector driven by a first drive frequency and a second acousto-optic deflector driven by a second drive frequency; the apparatus described above or herein to control said acousto-optic lens; microscope optics; a laser for supplying said beam of electromagnetic radiation; wherein said controller is configured to: apply said first drive frequency to said first acousto-optic deflector; simultaneously apply said second drive frequency to said second acousto-optic deflector; and simultaneously cause said laser to supply said beam of electromagnetic radiation to the input aperture of said first acousto-optic deflector.

In another aspect, the invention includes methods that allow a look-up table or similar to be built up.

In one method of the invention, a method of preparing data useful for configuring an acousto-optic lens is provided. The method may comprise selecting a plurality of possible locations in space that a beam of electromagnetic radiation can be deflected toward using the acousto-optic lens; determining, for each of said possible locations in space, a group comprising a plurality of pairs of candidate drive frequencies, each pair of candidate drive frequencies consisting of a first candidate drive frequency for said first acousto-optic deflector and a second candidate drive frequency for said second acousto-optic deflector, said pairs being such that if said first and second candidate drive frequencies of said pair were applied at the same time to said respective first and second acousto-optic deflectors, said beam of electromagnetic radiation would point toward said possible location in space; determining, for each pair of candidate drive frequencies in said group, an efficiency of transmission of said beam of electromagnetic radiation through said acousto-optic lens; and selecting as preferred a pair of candidate drive frequencies from said group in accordance with the determined efficiency for each pair of candidate drive frequencies.

Said selecting step optionally comprises: selecting, from said group of pairs of candidate drive frequencies, the pair of candidate drive frequencies that will cause said beam of electromagnetic radiation to be transmitted through said acousto-optic lens at the highest efficiency of all the pairs of candidate drive frequencies in said group.

In a further aspect, a method of configuring an acousto-optic lens for manipulating a beam of electromagnetic radiation so as to point at a desired location in space is provided. Preferably, the acousto-optic lens comprises at least a first acousto-optic deflector driven by a first drive frequency and a second acousto-optic deflector driven by a second drive frequency. The method may comprise determining a group comprising a plurality of pairs of candidate drive frequencies, each pair of candidate drive frequencies consisting of a first candidate drive frequency for said first acousto-optic deflector and a second candidate drive frequency for said second acousto-optic deflector, said pairs being such that if said first and second candidate drive frequencies of said pair were applied at the same time to said respective first and second acousto-optic deflectors, said beam of electromagnetic radiation would point at said desired location in space; determining, for each pair of candidate drive frequencies in said group, an efficiency of transmission of said beam of electromagnetic radiation through said acousto-optic lens; and selecting a pair of candidate drive frequencies from said group in accordance with the determined efficiency for each pair of candidate drive frequencies.

The selecting step optionally comprises selecting, from said group of pairs of candidate drive frequencies, the pair of candidate drive frequencies that will cause said beam of electromagnetic radiation to be transmitted through said acousto-optic lens at the highest efficiency of all the pairs of candidate drive frequencies in said group.

The invention also includes a method of configuring an acousto-optic lens for manipulating a beam of electromagnetic radiation so as to scan along a scan path, said acousto-optic lens comprising at least a first acousto-optic deflector driven by a first drive frequency and a second acousto-optic deflector driven by a second drive frequency, said method comprising: determining a reference point along said scan path; determining a group comprising a plurality of pairs of reference point candidate drive frequencies, each pair of reference point candidate drive frequencies consisting of a first reference point candidate drive frequency for said first acousto-optic deflector and a second reference point candidate drive frequency for said second acousto-optic deflector, said pairs being such that if said first and second reference point candidate drive frequencies of said pair were applied at the same time to said respective first and second acousto-optic deflectors, said beam of electromagnetic radiation would point at said reference point; selecting a pair of reference point candidate drive frequencies from said group based on a known efficiency of transmission of said beam of electromagnetic radiation through said acousto-optic lens for said reference point.

Said reference point preferably lies at the midpoint of said scan path.

Said step of selecting a pair of reference point candidate drive frequencies optionally comprises: selecting, from the pairs of reference point candidate drive frequencies in said group, the pair of reference point drive frequencies that will cause said beam of electromagnetic radiation to be transmitted through said acousto-optic lens at the highest efficiency of all the identified pairs of reference point drive frequencies.

Said selecting step optionally comprises: for each pair of reference point candidate drive frequencies in said group, determining a plurality of pairs of scan path drive frequencies associated with said scan path; determining, for each pair of scan path drive frequencies, an efficiency of transmission of said beam of electromagnetic radiation through said acousto-optic lens; selecting at least one pair of scan path drive frequencies from said group in accordance with the determined efficiency for each pair of scan path drive frequencies; and selecting the pair of reference point candidate drive frequencies from said group based on the selected pair(s) of scan path drive frequencies.

Said step of selecting at least one pair of scan path drive frequencies from said group optionally comprises: selecting, the pairs of scan path drive frequencies associated with a single pair of reference point candidate drive frequencies that will cause said beam of electromagnetic radiation to be transmitted through said acousto-optic lens at an efficiency exceeding a predetermined lower threshold for the duration of said scan.

Said step of selecting at least one pair of scan path drive frequencies from said group optionally comprises: selecting the pairs of scan path drive frequencies associated with a single pair of reference point candidate drive frequencies that will cause said beam of electromagnetic radiation to be transmitted through said acousto-optic lens with a highest to lowest efficiency ratio that does not exceed a certain predetermined threshold for the duration of said scan.

Said acousto-optic lens optionally additionally comprises a third acousto-optic deflector driven by a third drive frequency and a fourth acousto-optic deflector driven by a fourth drive frequency; said method additionally comprising: determining a second group comprising a plurality of pairs of candidate drive frequencies, each pair of candidate drive frequencies consisting of a third candidate drive frequency for said third acousto-optic deflector and a fourth candidate drive frequency for said fourth acousto-optic deflector, said pairs being such that if said third and fourth candidate drive frequencies of said pair were applied at the same time to said respective third and fourth acousto-optic deflectors, said beam of electromagnetic radiation would point at said desired location in space; determining, for each pair of candidate drive frequencies in said second group, an efficiency of transmission of said beam of electromagnetic radiation through said acousto-optic lens; and selecting a pair of candidate drive frequencies from said second group in accordance with the determined efficiency for each pair of candidate drive frequencies.

Generally, all of the disclosed methods and apparatus for deflecting a beam in one direction can be repeated for an orthogonal direction to convert a cylindrical lens into a spherical lens.

The invention includes apparatus for controlling an acousto-optic lens for manipulating a beam of electromagnetic radiation so as to point at a desired location in space, said acousto-optic lens comprising at least a first acousto-optic deflector driven by a first drive frequency and a second acousto-optic deflector driven by a second drive frequency, said apparatus comprising: a controller configured to determine a group comprising a plurality of pairs of candidate drive frequencies, each pair of candidate drive frequencies consisting of a first candidate drive frequency for said first acousto-optic deflector and a second candidate drive frequency for said second acousto-optic deflector, said pairs being such that if said first and second candidate drive frequencies of said pair were applied at the same time to said respective first and second acousto-optic deflectors, said beam of electromagnetic radiation would point at said desired location in space; said controller being configured to determine, for each pair of candidate drive frequencies in said group, an efficiency of transmission of said beam of electromagnetic radiation through said acousto-optic lens; and said controller being configured to select a pair of candidate drive frequencies from said group in accordance with the determined efficiency for each pair of candidate drive frequencies.

Said controller is optionally configured to: select, from said group of pairs of candidate drive frequencies, the pair of candidate drive frequencies that will cause said beam of electromagnetic radiation to be transmitted through said acousto-optic lens at the highest efficiency of all the pairs of candidate drive frequencies in said group.

The invention also includes apparatus for controlling an acousto-optic lens for manipulating a beam of electromagnetic radiation so as to scan along a scan path, said acousto-optic lens comprising at least a first acousto-optic deflector driven by a first drive frequency and a second acousto-optic deflector driven by a second drive frequency, said apparatus comprising: a controller configured to determine a reference point along said scan path; said controller being configured to determine a group comprising a plurality of pairs of reference point candidate drive frequencies, each pair of reference point candidate drive frequencies consisting of a first reference point candidate drive frequency for said first acousto-optic deflector and a second reference point candidate drive frequency for said second acousto-optic deflector, said pairs being such that if said first and second reference point candidate drive frequencies of said pair were applied at the same time to said respective first and second acousto-optic deflectors, said beam of electromagnetic radiation would point at said reference point; said controller being configured to select a pair of reference point candidate drive frequencies from said group based on a known efficiency of transmission of said beam of electromagnetic radiation through said acousto-optic lens for said reference point.

The reference point preferably lies at the midpoint of said scan path.

Optionally, said controller is configured to: select, from the pairs of reference point candidate drive frequencies in said group, the pair of reference point drive frequencies that will cause said beam of electromagnetic radiation to be transmitted through said acousto-optic lens at the highest efficiency of all the identified pairs of reference point drive frequencies.

Optionally, said controller is configured to: for each pair of reference point candidate drive frequencies in said group, determine a plurality of pairs of scan path drive frequencies associated with said scan path; determine, for each pair of scan path drive frequencies, an efficiency of transmission of said beam of electromagnetic radiation through said acousto-optic lens; select at least one pair of scan path drive frequencies from said group in accordance with the determined efficiency for each pair of scan path drive frequencies; and select the pair of reference point candidate drive frequencies from said group based on the selected pair(s) of scan path drive frequencies.

Optionally, said controller is configured to: select, the pairs of scan path drive frequencies associated with a single pair of reference point candidate drive frequencies that will cause said beam of electromagnetic radiation to be transmitted through said acousto-optic lens at an efficiency exceeding a predetermined lower threshold for the duration of said scan.

Said controller is optionally configured to: select the pairs of scan path drive frequencies associated with a single pair of reference point candidate drive frequencies that will cause said beam of electromagnetic radiation to be transmitted through said acousto-optic lens with a highest to lowest efficiency ratio that does not exceed a certain predetermined threshold for the duration of said scan.

Said acousto-optic lens optionally additionally comprises a third acousto-optic deflector driven by a third drive frequency and a fourth acousto-optic deflector driven by a fourth drive frequency; said controller being additionally configured to: determine a second group comprising a plurality of pairs of candidate drive frequencies, each pair of candidate drive frequencies consisting of a third candidate drive frequency for said third acousto-optic deflector and a fourth candidate drive frequency for said fourth acousto-optic deflector, said pairs being such that if said third and fourth candidate drive frequencies of said pair were applied at the same time to said respective third and fourth acousto-optic deflectors, said beam of electromagnetic radiation would point at said desired location in space; determine, for each pair of candidate drive frequencies in said second group, an efficiency of transmission of said beam of electromagnetic radiation through said acousto-optic lens; and select a pair of candidate drive frequencies from said second group in accordance with the determined efficiency for each pair of candidate drive frequencies.

The invention further includes a microscope system comprising: a controller apparatus; said acousto-optic lens; microscope optics; a laser for supplying said beam of electromagnetic radiation.

The controller apparatus can be any of the apparatus as described above and herein.

The invention further includes a method of configuring an acousto-optic lens for manipulating a beam of electromagnetic radiation so as to be deflected toward a desired location in space, said acousto-optic lens comprising at least a first acousto-optic deflector driven by a first drive frequency and a second acousto-optic deflector driven by a second drive frequency, said method comprising: selecting first and second drive frequencies in accordance with detailed efficiency data such that said selected first and second drive frequencies are within 1 MHz of the most efficient possible drive frequencies for a predetermined voxel of at least 50% of mini-scans forming the final image.

The invention also includes a method of configuring an acousto-optic lens for manipulating a beam of electromagnetic radiation so as to be deflected toward a desired location in space, said acousto-optic lens comprising at least a first acousto-optic deflector driven by a first drive frequency and a second acousto-optic deflector driven by a second drive frequency, said method comprising: selecting first and second drive frequencies in accordance with detailed efficiency data such that said selected first and second drive frequencies result in a transmission efficiency that is within 10% of the highest efficiency possible for a predetermined voxel of at least 50% of mini-scans forming the final image.

The detailed efficiency data can be data of efficiency of transmission for at least nine different beam positions. It may be manipulated and transformed and may be represented as frequency data, offset data or as raw transmission efficiency data. Preferably 50% of scans used to make a final image are configured using the method. However, 70%, 90% or 100% of scans can be so configured.

The controller of the present invention may take any suitable form, including being embodied by software running on a general purpose computer or as bespoke hardwired electronics or other control chips. The purpose of the controller is typically to provide the correct signals to the AODs to ensure that the beam is appropriately deflected. The controller may also process the image data, although this is not essential.

The present invention will now be further described, by way of non-limitative example only, with reference to the accompanying schematic drawings, in which:—

Figure 8:
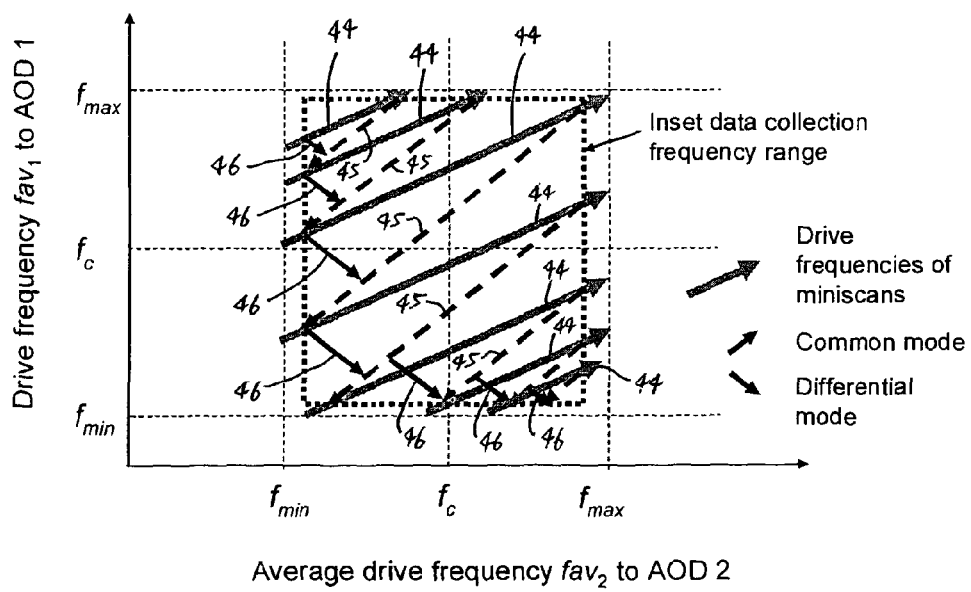
Figure 9:
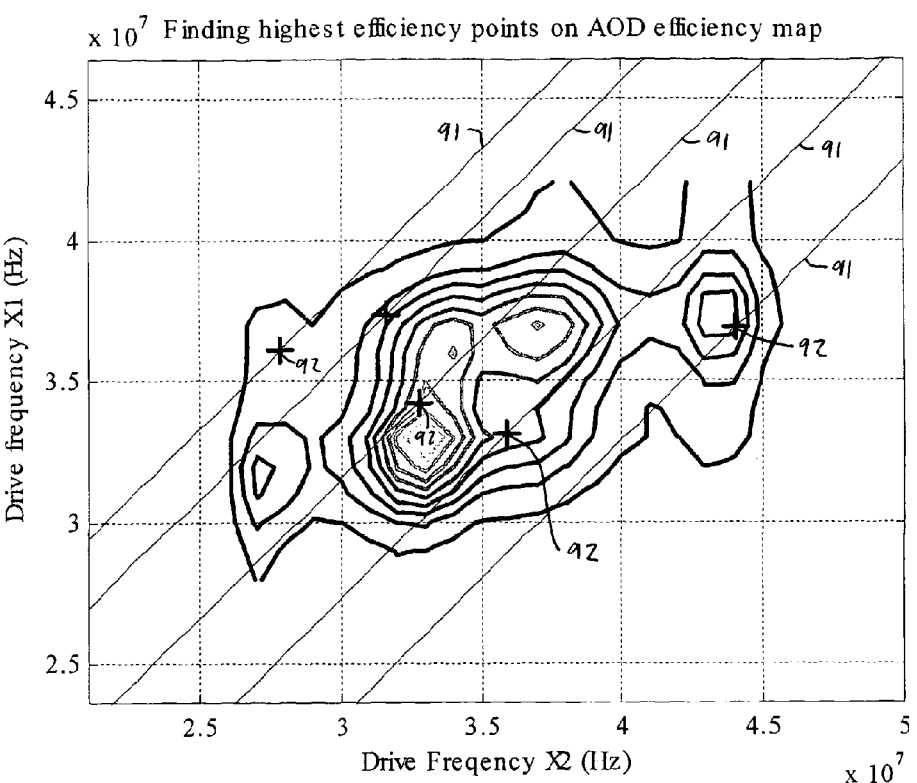
Figure 10:
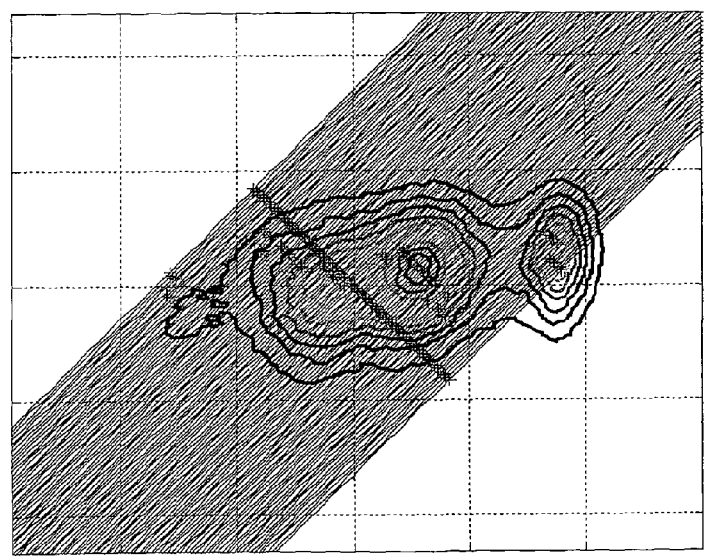
Figure 11:
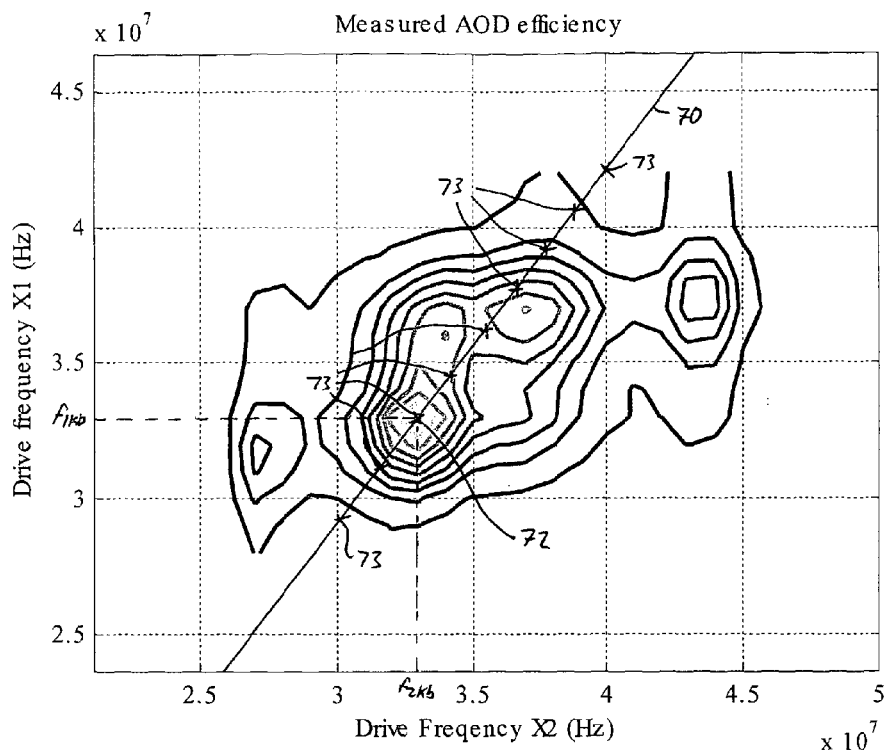
Figure 12:
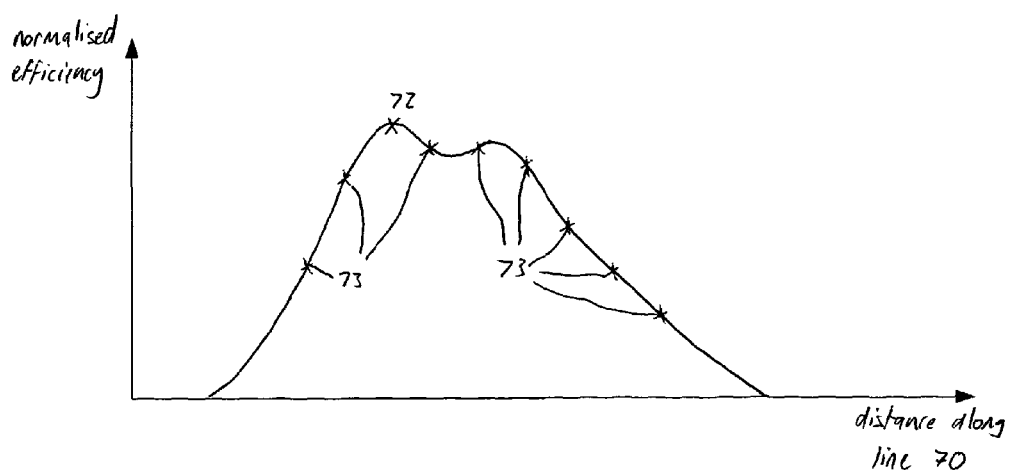
Figure 13:
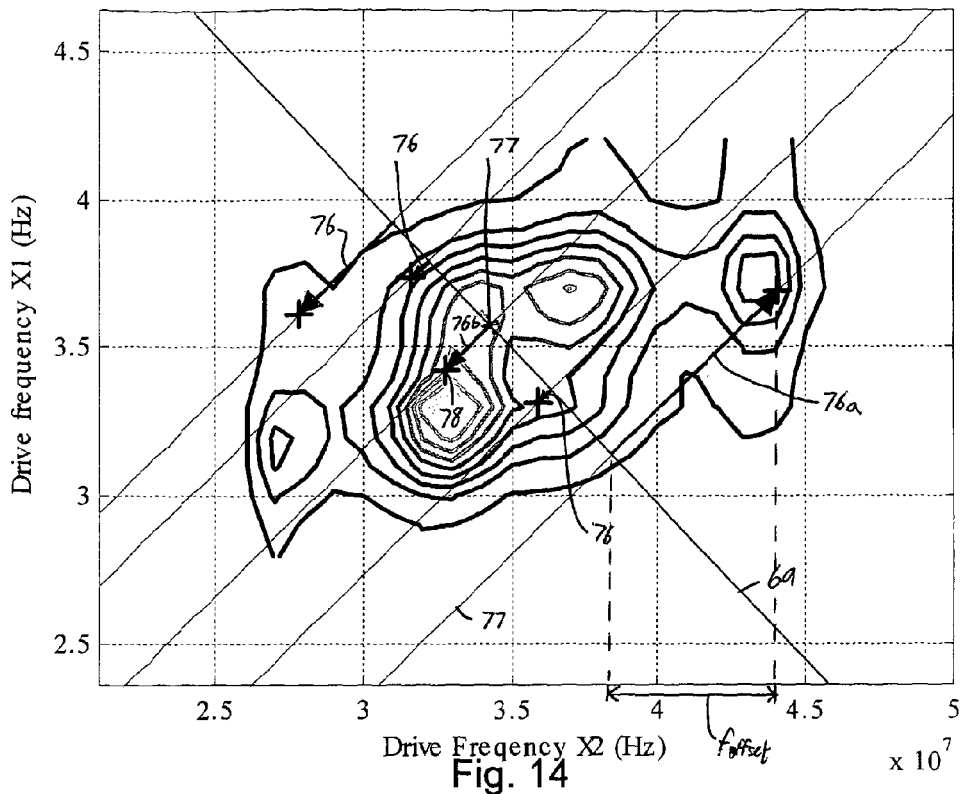
Figure 14:
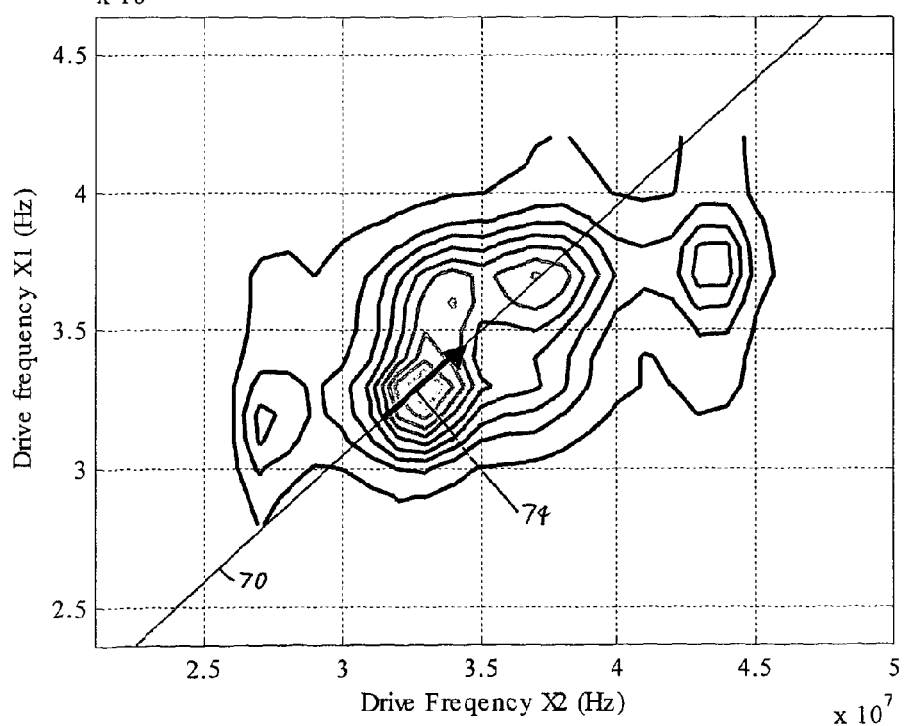
Figure 15:
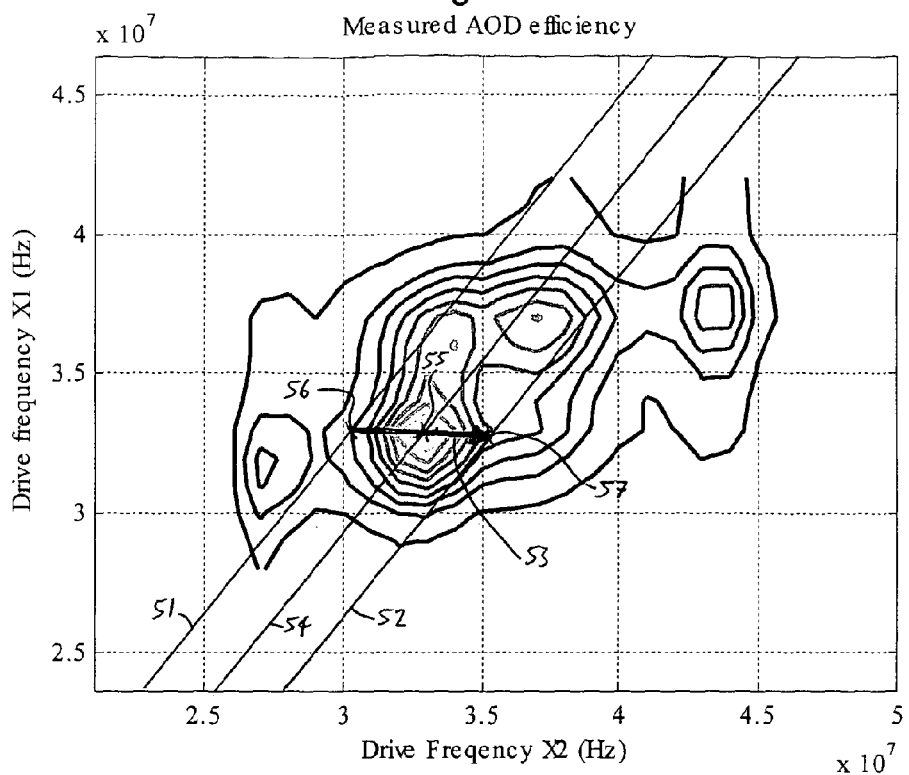
Figure 16:
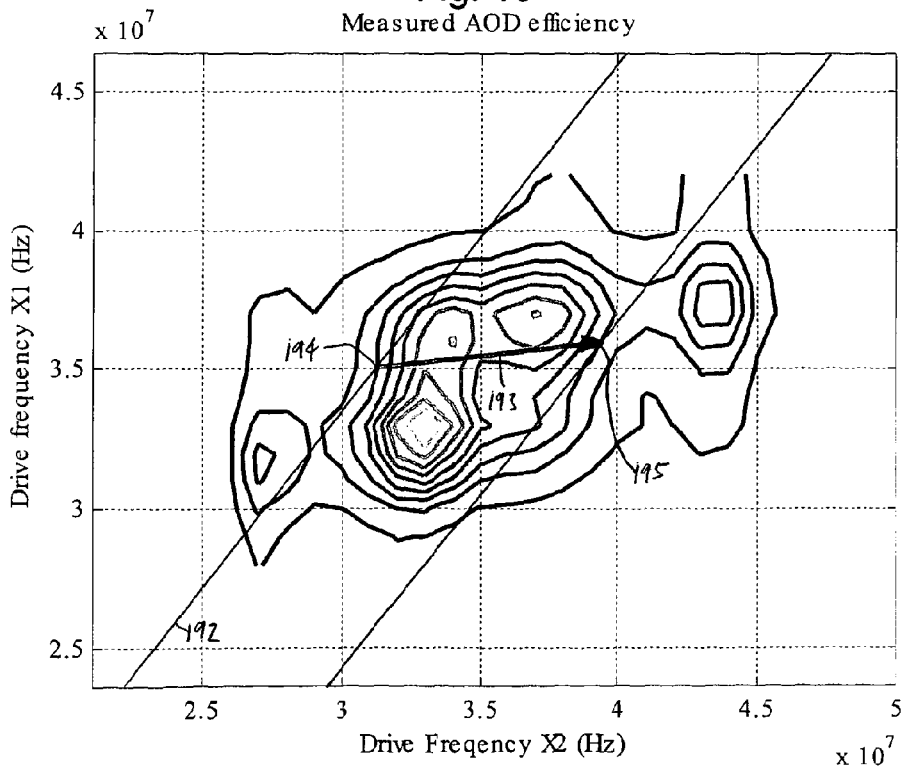
Figure 17:
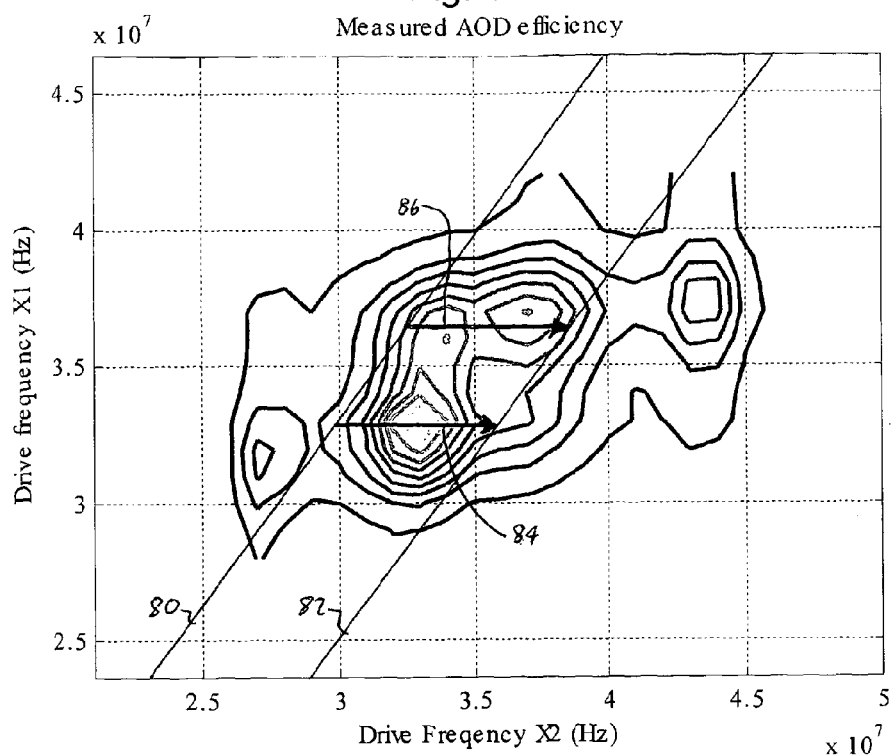
Figure 18:
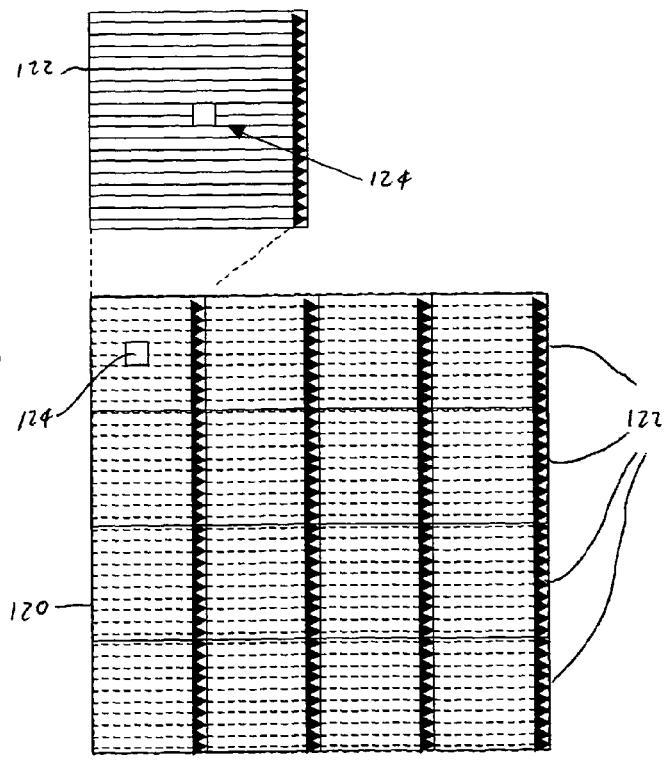

FIG. 8 again plots the drive frequency of the first AOD against the drive frequency of the second AOD and shows how the frequency limits and mini-scans can be visualised;

FIG. 9 shows the result of an experiment to determine the overall optical transmission efficiency of an acousto-optic lens for different combinations of drive frequencies for the first and second AODs;

FIG. 10 is similar to FIG. 9, but shows how the transmission efficiency varies with drive frequency for the third and fourth AODs;

FIG. 11 is useful for explaining a strategy to optimise the frequencies used in the pointing mode;

FIG. 12 is a graph of how efficiency of transmission of the AOL varies along line 70 of FIG. 11;

FIG. 13 is useful for explaining common mode offsets, that may be stored in a look up table to reduce the amount of calculation needed;

FIG. 14 is useful for explaining a strategy to optimise the frequencies used in the pointing mode when Z is non-zero;

FIG. 15 is useful for explaining a strategy to optimise the frequencies used in the scanning mode;

FIG. 16 is useful for explaining another strategy to optimise the frequencies used in the scanning mode;

FIG. 17 is useful for explaining yet another strategy to optimise the frequencies used in the scanning mode;

FIG. 18 shows how the field of view may be tiled so that preferred frequency pairs or common mode offsets for an area of volume may be stored in a look-up table;

FIG. 19 shows the images obtainable when one uses fixed drive frequency limits, as depicted in FIG. 8; and FIG. 20 shows the images obtainable when one uses the optimised frequency limits of the present invention.

The present invention is an improvement to the apparatus and methods described in WO 2008/032061 and may be implemented together with any of the measures discussed in WO 2008/032061, including but not limited to the compact configuration of AODs (including optional half wave plates and polarisers), the means for chromatic aberration correction and the different upstream and downstream AOD structures (including the $TeO_2$ crystals). Also, the equations for calculating the required drive frequencies disclosed in WO 2008/032061 are applicable to the present invention. The entire disclosure of WO 2008/032061 is hereby incorporated by reference. The terminology of WO 2008/0320061 has been adopted herein. For example $a_1$ denotes the frequency ramp rate of the drive signal applied to the first AOD.

Although the invention will be described with reference to the compact AOD configuration and its corresponding drive equations, the invention is equally applicable to other AOD configurations, such as configurations where telecentric relays are used to connect the AODs together. The general equations for driving such telecentrically connected configurations are simpler than for the compact configuration and are known to those skilled in the art.

The invention may be practised to manipulate any beam of electromagnetic radiation, but is preferably practised on a laser beam. As in WO 2008/032062, typical laser wavelengths of 700-1000 nm are used, but this does not limit the present invention. The centre frequency of the laser may lie in the range 200 to 2000 nm, preferably 400 to 1200 nm, more preferably 700 to 1000 nm, more preferably still being approximately 850 nm. The laser is typically pulsed, with the pulses having a length of 2 μs or less, preferably 500 fs or less, more preferably 100 fs or less.

Figure 1:
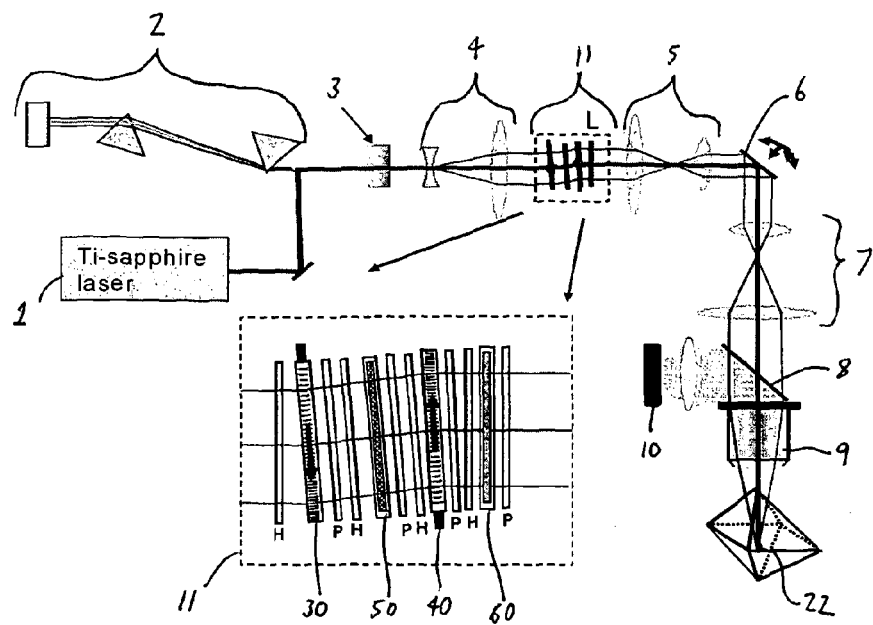
FIG. 1 shows the main components of a microscopy system for implementing the drive frequency algorithms of the present invention.
Figure 2:
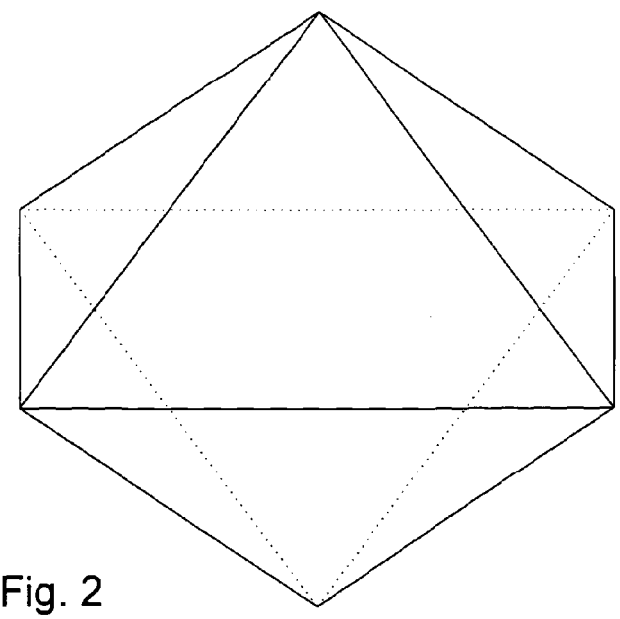
FIG. 2 shows the octahedral field of view obtainable with a prior art microscope.

FIG. 1 shows a schematic diagram of the complete apparatus that can be used to perform microscopy, preferably 2-photon microscopy. The present invention is concerned in particular with the method of driving the two or four AODs to give the improved results in terms of image quality. The invention preferably comprises a computer control system (not shown in Figures) that drives the AOL 11 based on the equations appropriate to the configuration of AODs.

With the exception of the prechirper 2, the other components of the complete 2-photon microscope shown in FIG. 1 are generally similar to those of a standard 2-photon microscope although the drive electronics for the AODs and image reconstruction is somewhat more complex than the galvanometer equivalent.

The laser 1 is preferably a Ti-sapphire laser but any laser may be used according to the experiments to be carried out. The laser preferably emits radiation in very narrow pulses, for example of the order of 100 fs, as disclosed in WO 2008/032061.

The prechirper 2 is preferably included to compensate for the effect of the high chromatic dispersion of $TeO_2$ which otherwise spreads out the laser pulses in time and greatly reduces 2-photon emission efficiency (Reddy, Kelleher et al. 2008).

A pockels cell 3 is optionally used to provide control over the laser intensity and a beam expander 4 may be used to expand the beam diameter prior to passing through the AOL 11. Although four AODs are shown in the AOL of FIG. 1, only two may be used if deflection in only one direction (e.g. the X direction) is desired.

The beam of electromagnetic radiation may exit the AOL through a relay 5 and may be deflected by optional galvanometer mirrors 6, whereafter it may pass through another relay 7 (comprising a field lens and a tube lens in this example) before reaching the microscope objective lens 9.

The objective lens 9 typically focuses the beam to the desired location and any reflected or scattered light preferably passes back up through the objective lens 9 and is routed by optional dichroic mirror 8 to the sensor 10, here in the form of a photomultiplier. The data acquisition from the photomultiplier tubes is typically precisely synchronised with the drive to the AODs so that for each data gathering timeslot (typically 1-4 μs long) the computer is able to insert into the computer memory the measured light intensity at the 3D coordinates of the voxel that the AOL is pointing to during that time.

Figure 4:
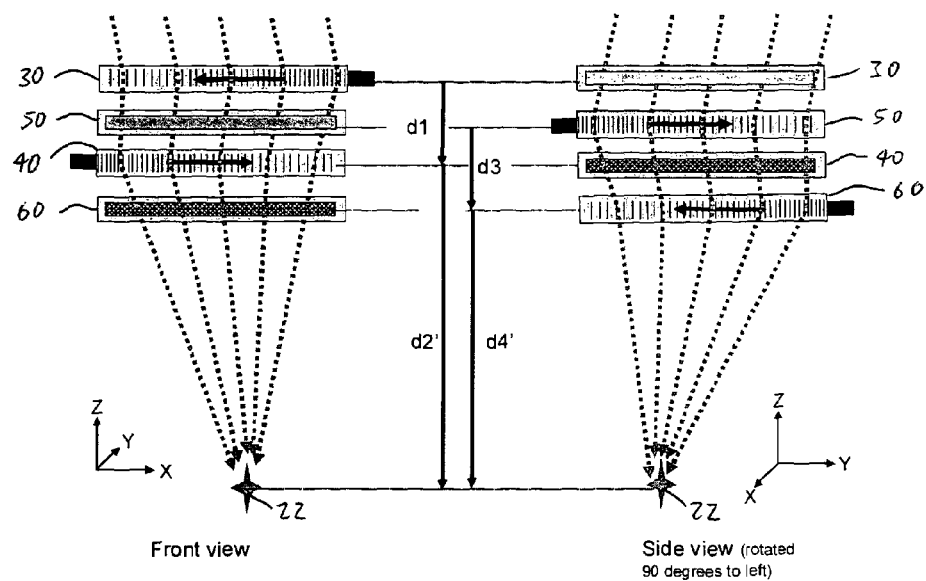
FIG. 4 shows two orthogonal views of a four AOD compact configuration preferably used in conjunction with the present invention.

FIG. 4 shows the sequence and orientation of four AODs forming an AOL. The first AOD 30 works together with the second AOD 40 to provide defection in the X direction. The first and second AODs are preferably arranged so that the acoustic waves in each travel in opposite directions (shown by arrows in FIG. 4). The third AOD 50 works together with the fourth AOD 60 to provide deflection in the Y direction. The third and fourth AODs are preferably arranged so that the acoustic wave in each travels in an opposite direction. Also, the acoustic waves in the third and fourth AODs are each preferably perpendicular to the acoustic waves in the first and second AODs. In the compact configuration shown, the AODs are in the order (form upstream to downstream in terms of the beam direction) first, third, second, fourth. As discussed in WO 2008/032061, this is a beneficial construction in terms of matching the polarisation of light between the AODs with minimal correction/filtering required by way of half-wave plates and/or polarisers. FIG. 4 does not show the half-wave plates (H) and polarisers (P) but these are shown in FIG. 1 and explained in more detail in WO 2008/032061. Alternatively, the AODs can be arranged in the order first, third, fourth, second, as disclosed in WO 2010/076579.

The present invention may equally be applied to a system having only two AODs, for example a system having only a first AOD and second AOD to provide defection in the X direction. Such a configuration would have a first AOD followed by a second AOD, with a half-wave plate to match the diffracted output polarisation of the first AOD to the required input polarisation of the second AOD, and a polariser to suppress the non diffracted light from the first AOD. Of course such a system can only deflect in the X direction and to avoid astigmatism can only focus on same Z plane that the YZ plane is focussed upon.

FIG. 4 shows two orthogonal views of a four AOD system. The third AOD 50 and fourth AOD 60 are interleaved with the first AOD 30 and second AOD 40 as shown, the distance between the third AOD 50 and fourth AOD 60 being $d_3$ and the distance from the fourth AOD 60 to the focal point being $d'_4$. As disclosed in WO 2008/032061, the frequency ramp rates to apply to the drive signals for driving this configuration so as to focus light at any desired point in the field of view can be calculated.

The first and second AODs 30, 40 focus in the chosen X-Z plane whilst the third and fourth AODs 50, 60 focus in the Y-Z plane. The distances $d'_2$ and $d'_4$ are preferably such as to ensure that the final focus is the same in both planes. Any error will in general cause astigmatism. In such cases, small corrections may be applied to the ratio of the X ramp rate to the Y ramp rate to fine tune the astigmatism of the focus. This is equivalent to adjusting the ratio of $d'_2$ to $d'_4$ so that the Z value of the focal position in the X-Z and X-Y planes is the same. These fine tuning corrections may be a function of the Z position of the focal spot and can readily be built into the algorithms that compute the ramp rate of the AODs before each scan. Such fine tuning is, however, not essential.

As disclosed in WO 2008/032061, the actual distances between the AODs and the optical thickness of any intervening components, as well as the AODs themselves, needs to be taken into account when determining $d_1$, $d_2$, $d_3$, $d'_2$ and $d'_4$. If further optical components are interposed between the AODs, such as half wave plates and polarisers, then the apparent optical separation Scan be calculated by taking into account the refractive index of such additional components. Also, the refractive index of the AODs themselves is taken into account. This can be done by assuming that the acoustic wave enters and leaves the AOD at its thickness-midpoint such that the apparent optical distance $d_1$ is equal to the distance in air between the AODs plus half the thickness of AOD1 divided by its refractive index plus half the thickness of AOD2 divided by its refractive index. When the two AODs are identical, then the value $d_1$ equals the distance in air plus the thickness of the AOD divided by its refractive index.

In theory the compact configuration of AOL can be used to achieve a stationary focal point at any chosen value of Z within the field of view.

As well as being applicable to the pointing mode (where light is focused to a stationary point), the invention is also applicable to the scanning mode, which in general requires precise control of X and Y plane scan rate at a fixed Z plane. The fact that the AODs have a limited operating frequency range and the frequency ramp rates for Z focusing are high, means that it is often necessary to reset the drive frequencies to the other side of the operating frequency range. How to do this to achieve mini-scans is disclosed in WO 2008/032061.

Figure 5:
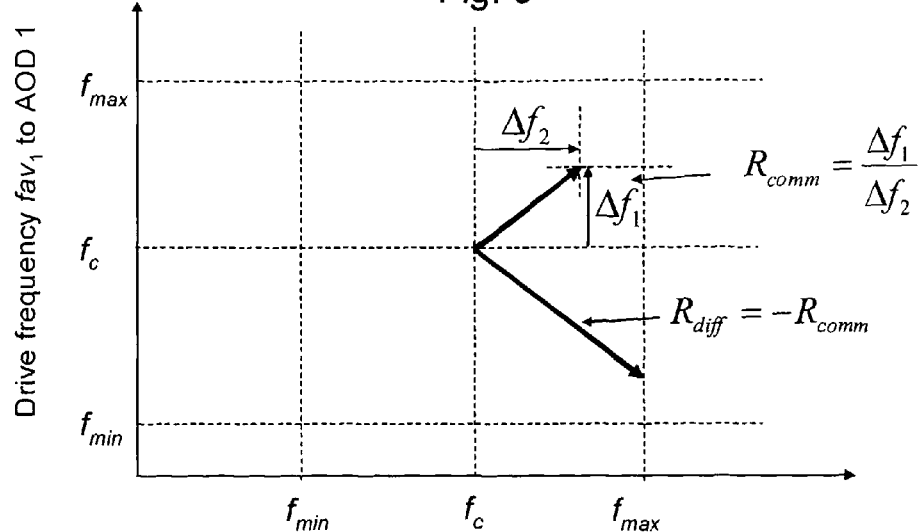
FIG. 5 is a graph plotting the drive frequency of the first (upstream) AOD along the ordinate and the drive frequency of the second (downstream) AOD along the abscissa.

For the case of X-Z deflection and focusing with the first and second AODs 30, 40, the average drive frequencies $fav_2$ and $fav_1$ can be plotted on the X and Y axes of a graph as illustrated in FIG. 5. These 'f average' symbols represent the frequency at the centre of the AOD at the particular time being considered. As the ramp rates $a_1$ and $a_2$ are linear in both time and space, the frequencies at the centre are the spatial averages of the frequencies currently in the AOD aperture and in turn determine the average deflection angle of the AOD. Referring again to FIG. 5, any pair of average frequencies can be represented on this plot by a point in the $fav_2$, $fav_1$ plane. A gradual or step change in the pair of drive centre frequencies can be represented by a vector lying in the plane. Its direction determines what happens to the focal spot position. If $fav_2$ and $fav_1$ are changed with a differential gradient marked as common mode drive gradient $R_{comm}$, there is no change in the position of the spot. Common mode drive frequency change is defined as change where the ratio of the frequency changes is:

$$R_{comm} = \frac{\Delta fav_1}{\Delta fav_2} = \frac{2d_2'}{2d_2' + d_1}$$

Notice that this ratio of frequency change is exactly the ratio of ramp rates that gives a stationary focal spot at a distance $d'_2$ from the last AOD. It has a fixed value for any particular chosen Z focal plane. For a stationary focal spot, if one plotted the two frequencies at the centre of the two AODs as they varied with time, they would move along a line parallel to the vector shown. This result shows that the focal spot will be at the same position in space for any pair of frequencies lying on the common mode deflection line.

The converse applies to the differential mode line on this plot defined by:

$$R_{diff} = \frac{\Delta fav_1}{\Delta fav_2} = \frac{-2d_2'}{2d_2' + d_1}$$

Figure 6:
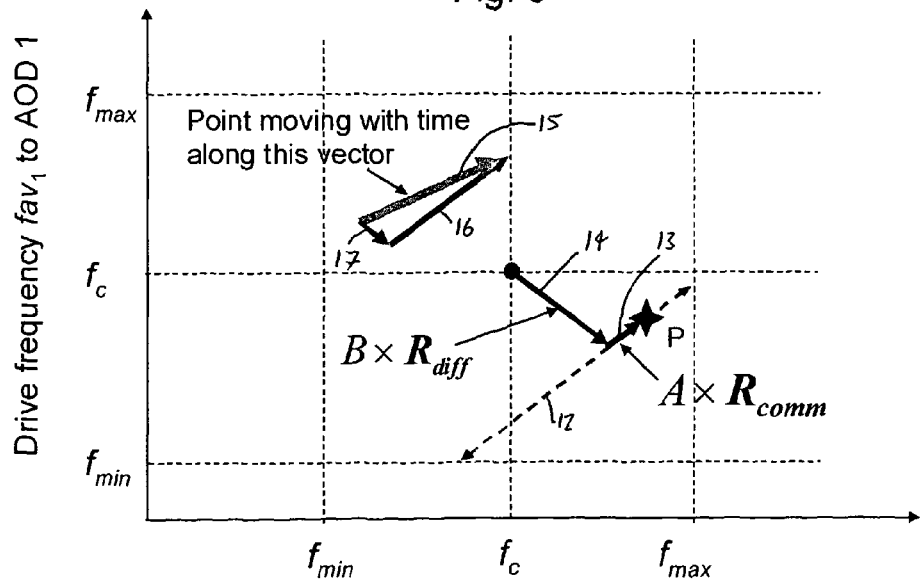
FIG. 6 is a graph similar to FIG. 5 and shows how a general scan may be composed of a common vector and a differential vector.

Changes in this direction produce changes in X position of the focal spot with no changes in common mode frequency difference. Its gradient is by definition −1 times the common mode gradient. Referring to FIGS. 5 and 6, in $fav_2,fav_1$ frequency space the vectors $R_{comm}$=[1, $R_{comm}$] and $R_{diff}$=[1, $R_{diff}$] (where vectors are shown in bold and scalars in normal type face) can be used as the unit vectors of a 2D basis. Any general vector in this plane can therefore be analysed in terms of its common mode and differential mode basis vector components.

The point 'P' in FIG. 6 represents a particular $fav_2$, $fav_1$ coordinate. This can equally well be represented by the vector equation $$[fav_1, fav_2] = [f_c, f_c] + A \times R_{comm} + B \times R_{diff}$$

Where $f_c$ is the centre frequency of the AOD drive range and A and B are the scalar multipliers for the unit vectors pointing in the $R_{comm}$ and $R_{diff}$ directions as illustrated by the arrows 13, 14 on the figure. The dotted line 12 through the point 'P' with a gradient $R_{comm}$ (scalar) is the common mode line of all the other points that equally well would point at the same physical position. For planes where Z≠0, a ramp rate must be applied to the AODs, meaning that the frequency must constantly increase or decrease with time. Thus, when focussing at a fixed physical location, the point P in frequency space moves along the common mode line $R_{comm}$. Using this plot it can be seen that for repeated pointing at the same position in 3D space that point P points at, without the drive frequencies going outside the high efficiency regions of the AODs, the ramps must repeatedly start at the pair of frequencies defined by the lower left end of the dotted blue line and stop at the top right end. In jumping back to the start, there is no shift in the position the AODs are pointing at.

FIG. 6 also shows a line 15 representing a time sequence of [$fav_2$, $fav_1$] coordinates. These can also be analysed into their $A \times R_{comm} + B \times R_{diff}$ pairs as shown by lines 16 and 17. In this case the line 15 is the drive to produce a focused beam with a small differential component that means the spot is slowly moving in the X direction. The common mode scan rate in time determines the Z focal plane (and the precise direction of the $R_{comm}$ and $R_{diff}$ unit vectors on this plot) as shown by lines 16 and 17.

In general, FIG. 6 shows how any pair of frequencies or difference in pair of frequencies vector can be analysed into common mode and differential mode components. Bold text refers to a vector, normal text to a scalar. The dotted line represents all pairs of frequencies between the AOD drive limit frequencies that cause the beam to point at the point P. Driving the AODs repetitively up this line and jumping back to the lower position corresponds to the sawtooth of frequencies required to focus on a single spot in the same lateral offset (X) that the static frequency pair at P would point. The rate of shift along the line determines the focus (Z) and the precise direction of this common mode line. The vector denoted as 15 in FIG. 6 combines a large common mode 16 with a small differential mode 17 and steady movement along this line 15 produces fixed Z focusing and relatively slow X translation of the focal point.

To build up a three-dimensional image of a semi transparent sample (such as brain tissue), it is useful to be able to follow a raster scan with the focal point along a predetermined path through the sample. The most commonly used raster scan is to move the focal point in the X direction, keeping the Y and Z values constant, to then increment the Y position by some small amount, to perform another scan in the X direction and so on until a two-dimensional grid of scans is achieved. The Z direction is then incremented and another two-dimensional grid is scanned until a three dimensional volume has been built up. This type of raster scanning is much faster than building up an image by using the pointing mode to sequentially address every point. The pointing mode takes one AOD fill time plus one data collection time (dwell time) to take data from each point. With 25 μs AOD fill time and a typical 4 s dwell time this process takes nearly 4 minutes in the pointing mode for the 7.8 million voxels that the target system is capable of resolving. With raster scanning many data points are gathered for each AOD fill time by moving the focused spot over sequential voxels at a rate of 1 dwell time per voxel. As the raster scans increase in length so the total scan time reduces asymptotically towards the limit of one dwell time per voxel which is about 30 seconds for 4 μs dwell time scanning the full 3D volume. Equations for such raster scanning were derived in WO 2008/032061 and reference is made to those.

Figure 7:
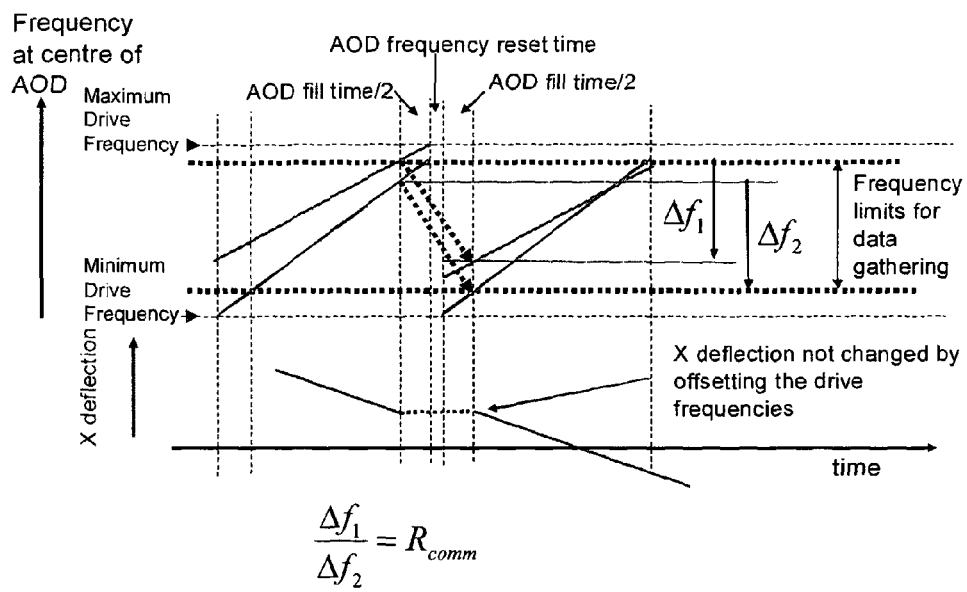
FIG. 7 is a graph of frequency against time showing how the frequencies applied to each AOD can be changed with time, so as to implement a series of mini-scans for planes where $Z \neq 0$.

The first AOD 30 is driven by a first drive signal and the second AOD 40 is driven by a second drive signal. These drive signals cause acoustic waves of the same frequency to be applied to the AOD aperture. FIG. 7 illustrates in the upper part the first and second drive signal frequencies vs. time for part of a sequence of mini-scans deflecting in X and focusing a focal spot at a constant Z plane across one line of a raster at fixed Y value. The lower part of FIG. 7 shows the deflection in the X direction as a function of time.

In order to produce the required focusing in Z the ramp rates on both AODs shown in FIG. 7 are relatively high. Since there is a limited frequency range, it is not possible to do a single scan right across the maximum possible X scan range.

The scanning process therefore has to be broken up into a sequence of mini-scans. Two of these mini-scan frequency traces are plotted in FIG. 7 showing the transition between them. The maximum and minimum drive frequencies for the AODs are arbitrarily defined in this case as a result of observations of where the efficiency drops below some percentage (e.g. 50%) of the peak efficiency. The maximum and minimum frequencies are respectively considered to be the same for both the first and second AODs.

It takes one AOD fill time for the sound wave to fill the AOD aperture so that data recording can begin, and the time at which a particular frequency reaches the mid point of the AOD is half the AOD fill time after it was transmitted by the transducer. Recording of data from a full AOD is therefore only possible for frequencies sent by the transducer more than half an AOD fill time from either the beginning or end of the frequency ramp. This further reduces the available frequency range as shown by the inset bold dotted lines in FIG. 7. The total time from the end of data gathering of one mini-scan to the start of data gathering of the next is thus the AOD fill time plus any 'flyback' time for electronically resetting the drive frequencies.

When calculating the precise start and stop frequencies of each mini-scan, the position of the focal spot at the start of the first voxel of a new mini-scan is arranged to be exactly in the same position as it was at the trailing edge of the last voxel of the previous mini-scan. This is illustrated in the lower part of FIG. 7. The frequency offsets $\Delta f_1$ and $\Delta f_2$ must typically (for the compact configuration) be in the exact ratio $R_{comm}$ to meet this condition. The line 48 shows that the X deflection at the end of one mini-scan is the same as the X deflection at the beginning of the next mini-scan. During the "fly-back period" between the end of one data gathering sequence and the beginning of the next, the line is shown dotted to denote that no data is gathered for this time period.

FIG. 8 illustrates in the $fav_2$-$fav_1$ jay plane the full sequence of mini-scans making up one full X scan. The arrows 44 correspond to the pair of drive frequencies 32, 42 at the centre of the AODs shown vs. time in FIG. 7. As the vector 44 has a small differential mode component it is scanning as well as focusing at a particular Z plane. This is shown by the differential mode lines 46. The frequency limits for data collection have to be inset with respect to the efficiency limits because data can only be gathered from full AODs. The common mode (shown dashed) fly-back lines 45 ensure that when data gathering starts again in the next mini-scan it does so from the same position. The start and stop frequencies of the mini-scans are defined by extending the ramps 44 out to the drive frequency limits as shown in FIG. 8.

As in the pointing mode, the precise direction of the common mode unit vector 45 and the differential mode unit vector 46 are dependent on the chosen focal Z plane.

The X scan rate $\delta\theta/\delta t$ is set at a rate so that it takes one dwell time to scan across one voxel. This is done by defining the semiscan angle of the AODs 's', Nvox, the number of voxels in the scan, typically 100 to 500 and the dwell time of the focal spot as it scans across each voxel.

The equations of WO 2008/032061 apply where there are two AODs for focusing in the X-Z plane or, as shown in FIG. 4, when there are four AODs. In this case, the angular scan rate $\delta\theta/\partial t$ is that measured about the second AOD 40. The apparent rate as measured about the fourth AOD 60 can be obtained by multiplying this scan rate by $d'_2/d'_4$.

The algorithms for performing these scans, based on fixed values for upper and lower frequencies $f_{max}$ and $f_{min}$, and using the equations of WO 2008/032061 are referred to as Absolute Frequency Limit (AFL) algorithms because they are based on the assumption that in order to keep the AOD efficiency high, each AOD must at all times stay within the absolute frequency limits set for the AODs. Surprisingly, it has been found that it is possible to scan a larger volume at high efficiency by abandoning fixed frequency limits and instead optimising the frequency limits independently for each point or for each mini-scan.

The present inventors have made many measurements of the individual AOD efficiency vs. drive frequency for the AOD configuration shown in WO 2008/032061. These measurements showed high efficiency over at least the 30 to 40 MHz drive frequencies corresponding to 6.5 mrad semiscan deflection angles for a fixed input angle. This lead to the concept of absolute frequency limits where $f_{min}$ is set to 30 MHz and $f_{max}$ is set to 40 MHz. Other AOD configurations can lead to different frequencies being identified.

These plots are however not sufficient to model the complete AOL performance as it has been found that it is the input acceptance angle of the second AOD in each pair that is actually the main limitation of the system. It is in practice difficult to make accurate high-speed measurements of the input acceptance angle of an AOD without using another AOD in front of it to make accurate fine deflections of the input beam.

In order to solve this difficulty, the inventors measured the performance of the complete AOL and used this information to deduce the performance of each AOD. The difficulty with this approach is that it is impractical to measure the optical power levels in between the AODs because there is insufficient space to place a large area detector there. For the measurements taken on the four-AOD configuration, the measurement obtained of overall AOL efficiency is the product of the efficiency of all four AODs in series. This potentially introduces uncertainty as to the root cause of any particular behaviour. However from a system perspective this is the performance that it is most important to understand. The measurement that has been found most useful is to plot beam transmission efficiency vs. the drive frequencies required for the first and second AODs at fixed third and fourth AOD drive frequencies (and vice versa). FIGS. 9 and 10 graphically show the result of this work.

FIG. 9 is a contour plot of efficiency of a complete Acousto-Optic Lens (AOL) as a function of the drive frequencies to the first and second AODs 30, 40 whilst the third and fourth AODs 50, 60 are driven at 35 MHz fixed frequencies. The contours are normalised 2-photon efficiency measured by scanning the focused spot through a fluorescent plastic slide (Chroma Technology Corp). The peak normalised intensity is 1 at the centre of the lightest (central) contour, and each contour is a step of 0.1. The outermost contour represents a 0.1 normalised intensity. Superimposed on the plot is a diagram to illustrate one computation that the new Optimised Frequency Limit (OFL) algorithm can do to improve, optimise or maximise efficiency for each mini-scan. The diagonal lines 91 contain the common mode drive frequencies that give the same X deflection in the Z=0 plane. The crosses 92 represent the point on each common mode line 91 where the transmission will have the highest efficiency. These crosses 92 lie over the "highest" contour for the common mode line 91 in question. In one scanning strategy, this pair of drive frequencies can be chosen for the one of the voxels (e.g. the centre voxel) of the mini-scan.

FIG. 10 is a contour plot of efficiency of the complete Acousto-Optic Lens (AOL) as a function of the drive frequencies to the third and fourth AODs 50, 60 whilst first and second AODs 30, 40 are driven at 35 MHz fixed frequencies. The contours are normalised 2-photon efficiency measured by scanning the focused spot through a fluorescent plastic slide (Chroma Technology Corp). The peak normalised intensity is 1 at the centre of the innermost contour, and each contour is a step of 0.1. Superimposed on the plot is a diagram to illustrate one computation the new (OFL) mini-scan algorithm can do to maximise efficiency for each mini-scan. 100 independent possible deflections are computed here, one for each line of the vertical scanning and used repeatedly for each mini-scan making up a particular Y full scan. The diagonal lines are the common mode drive frequencies that give the same Y deflection. The crosses represent the point on each common mode line where the transmission will have the highest efficiency. This pair of drive frequencies can be chosen for the one voxel (e.g. the centre voxel) of that Y scan in one scanning strategy.

FIG. 10 shows the same type of plot for the 2-photon efficiency of third and fourth AODs 50, 60, with the first and second AODs held at fixed frequency. This shows similar results but not such high efficiency at the lower end of the fourth AOD frequency range. This may be caused by non optimal fourth AOD alignment.

These contour plots were measured at high speed by scanning the second drive signal frequency over the full plotted range, and dividing the range into 100 pixels at 4 µs/pixel and stepping the first drive frequency by one hundredth of its full range after each line. There is a small correction on plotting the second drive signal frequency against its drive frequency data point to allow for the fact that the frequency at the centre of the AOD lags behind the frequency at the transducer by half the AOD fill time times the second AOD ramp rate.

Note that this contour plot shows that useful 2-photon efficiency (to the 0.2 normalised 2-photon efficiency contour) can be obtained for second AOD drive frequencies varying from 27 to 44 MHz corresponding to 11 mrad semiscan angle, whereas the frequency range for the first AOD is approximately 31 to 38 MHz corresponding to a semiscan angle of 4.5 mrad. Since we know that the high efficiency deflection angle of the first AOD is much larger than a 4.5 mrad semiscan angle, we can surmise (but not prove from this plot) that the reason for the limited range of high efficiency frequencies for the first AOD is the limited acceptance angle of the second AOD.

It is clear in both these plots that it is possible to drive the second AOD of each pair over a much wider range of frequencies than the first AOD and still find combinations of drive frequencies that give high efficiency. As will be shown in the results later, this enables the scan volume to change from the octahedral shape described so far to a cuboid of more than three times the volume.

These measurements, together with the understanding of common mode and differential mode frequency drive derived above, will be used to illustrate how the limitations of the fixed drive frequency limits can be overcome, leading to surprising improvements in field of view and patternation performance.

The Absolute Frequency Limit (AFL) algorithm discussed above operates by simply initially specifying the maximum and minimum drive frequencies it is permissible to drive any of the four AODs. In contrast, the new Optimised Frequency Limit (OFL) algorithm can select the frequencies to use to improve, optimise or maximise performance. In one embodiment, the algorithm carries out a computation that is equivalent to selecting mini-scan drive frequencies using a peak searching algorithm from the efficiency plots of FIGS. 9 and 10 to improve the overall diffraction efficiency of each mini-scan.

The invention includes several strategies for pointing or scanning as follows:

A. Pointing Mode—Maximum Possible Efficiency at Desired Location, Z=0

For a desired location in space inside the possible scan volume, there will in general be one common mode line for X deflection that defines all the candidate frequency pairs that could be used to deflect the beam to the desired location. The slope of the common mode line is dependent on the value of Z for the desired location.

According to this strategy, the point along this common mode line having the highest efficiency can be identified from FIG. 9 (in FIG. 9, the point along each common mode line 91 having the highest efficiency is marked with a cross 92) and the frequencies at this point can be used to deflect the beam.

An example will be described for the Z=0 plane. This plane is a special case because it is only in this plane that it is possible to deflect the beam to a fixed point and to keep the beam pointing there without needing to reset the AOD frequencies. The reason for this is that at Z=0, no ramps need to be applied to the AODs and merely fixed unchanging frequencies will cause the necessary deflection in X and/or Y.

For simplicity, a point at X=k, Y=0 and Z=0 will be chosen. This means that only the first and second AODs need to be used to provide the X deflection. If Y were non-zero, the same principles can be used to derive the frequencies for driving the third and fourth AODs to provide the Y deflection, but using the efficiency plot of FIG. 10 instead of FIG. 9.

The value k of X deflection determines the amount of offset needed between the first and second drive frequencies. This in turn leads to identification of the appropriate common mode line in FIG. 11 (which is the same plot as FIG. 9). Suppose the deflection of X=k is achievable with any of the frequencies lying along line 70 in FIG. 11. To maximise efficiency, the exact frequency pair to use can be selected by selecting a frequency pair that lies along the line 70 having the highest efficiency of all the pairs that lie on the line 70. This is illustrated in FIG. 12 where the efficiency of the frequency pairs lying along the line 70 is plotted. To obtain the best frequency pairs, the highest point in the plot of FIG. 12 is identified, here shown as point 72. The corresponding point is also shown in FIG. 11. Once this point is identified, it is simple to determine the values of frequency from FIG. 11 as $f_{1kb}$ and $f_{2kb}$. In this example, $f_1$ kb and $f_{2kb}$ are respectively each about 33 MHz. According to this strategy, the location in space k, 0, 0 will be pointed at using a first AOD drive frequency of $f_1$ kb and a second AOD drive frequency of $f_{2kb}$. In theory, the same location could have been obtained by using any of the other frequency pairs 73 lying along line 70. However, the pair corresponding to point 72 was used as this leads to the highest efficiency of transmission.

In practice, this strategy can be implemented in real time by firstly identifying a group comprising a plurality of pairs of drive candidate frequencies 72, 73. These candidate frequency pairs 72, 73 are the ones that will cause the desired X deflection and as such are the pairs of frequencies lying along common mode line 70 in the region of interest. The candidate pairs are shown as points 73 in FIG. 11.

Once the group containing the candidate pairs 73 has been determined, it is possible to use the data of FIG. 11 to determine the efficiency of transmission that each pair in the group would provide if the frequencies of the pair were to be used in the AODs. These efficiencies are shown graphically by numerals 72 and 73 in FIG. 12.

It is then possible to select a pair of frequencies to use based on the determined efficiencies. In this example, the highest efficiency is identified and the pair 72 of the group having the highest efficiency is used in the AODs.

The group may comprise any convenient number of frequency pairs, for example between 2 and 100 pairs, preferably between 5 and 50 pairs, more preferably between 5 and 20 pairs. Where smaller numbers of pairs are used, it is possible to use interpolation when deciding the exact frequencies to use.

Look-Up Table Method 1

The real-time processing power requirement can be reduced by pre-storing data related to the best frequency pair for a number of common mode lines in a look-up table. For example, for each of a range of values of Z (for e.g. 30 values), the best frequency pair for 30 or so common mode lines can be stored. This corresponds to 20×30=600 preferred frequency pairs or 20×30×2=1200 data locations for X, and another 1200 data locations for Y. In such a case, the following method can be used to determine the AOD drive frequencies to use.

For the point X=k, Y=0, Z=0, the appropriate section of the look up table can be consulted and a common mode line for which data is stored that lies closest to the true common mode line (that will give exactly the correct X deflection) can be identified. The preferred frequency pair can be looked up. If the table happens to include data for the exact common mode line of interest, then the preferred frequency pair can simply be used as the AOD drive frequencies.

If the table does not contain data for the common mode line of interest, then the preferred frequency pair for the nearest common mode line is obtained and then modified so as to cause the beam to point at the exact correct location.

Such correction can be achieved be adding or subtracting a differential mode component that shifts the frequencies to the correct common mode line. Alternatively, one or other of the first or second drive frequencies can be shifted until a point on the correct common mode line is achieved.

Look-Up Table Method 2

Instead of storing preferred frequency pairs themselves, it may be beneficial to instead store data that is related to preferred frequency pairs, such as data of common mode offsets. These offsets are illustrated as vectors 76 in FIG. 13.

Here, the differential mode line 69 passing through the point 35 MHz, 35 MHz is considered to be the origin of the coordinate system. Common mode offsets 76 are measured along a respective common mode line and give the amount of frequency shift required to reach the point in FIG. 13 of highest efficiency. For example, for common mode offset 76a, an amount $f_{offset}$ is stored, together with the value of the slope of the common mode line 77.

The data in the lookup table thus corresponds to a particular value of Z and provides a particular offset to the best frequency pair for each of a plurality of common mode lines.

The table is used as follows. Firstly, the known equations (see WO2008/032061) are used that take the desired location in space as an input and provide a point on the appropriate common mode line as an output. For example, for a location k, 0, 0, the equations will provide reference frequency pair 77 shown in FIG. 13.

The look-up table is then consulted and the common mode frequency offset data stored for a frequency location closest to point 77 is obtained. This offset data 76b is then applied to modify the reference frequency pair 77 to obtain the preferred frequency pair 78 that can be used as drive frequencies for the AODs.

As will be clear, the use of a look-up table can reduce the amount of real time processing required, although it does introduce a slight amount of error in selecting the best frequencies because some modification either of the stored preferred frequencies will be needed or some compromise in selecting the nearest common mode offset will be required.

B. Pointing Mode—Maximum Possible Efficiency at Desired Location, Z≠0

The pointing mode also includes the case where the physical location is not moved at all, but because Z≠0, mini-scans need to be used to reset the frequencies. This mode is actually conceptually very similar to the scanning mode that will be described later. In this explanation, "scanning" and "mini-scan" refer to any occasion where it is necessary to ramp the frequencies and so includes the pointing mode where Z≠0.

In this case, the method is similar to that disclosed above, but a reference location lying along the mini-scan route is identified and made to correspond with the point of highest efficiency. Preferably the point at the centre of the mini-scan is selected, although any point can in practice be used.

Suppose it is necessary to point to position X=k, Y=0, Z=m for 30 μs, where k and m are positions inside the scan volume. As Z≠0, it is necessary to ramp the frequencies while maintaining the necessary offset between the first and second drive frequencies to provide the correct X deflection. In practice, this means one needs to follow a vector 13 having a certain length (related to the Z position and the dwell time of 30 μs), as shown in FIG. 14. As can be seen from FIG. 14, there is a choice as to where the vector 74 is placed along common mode line 70. According to this strategy, the centre of vector 74 is selected as a reference point and is made to coincide with the highest efficiency point of line 70. This places the mini-scan vector in a region of operation that is known to be efficient, as shown in FIG. 14.

The two look-up table methods can equally be used as described above, but using the reference location instead of the desired location.

C. Scanning Mode—Maximum Possible Efficiency at Point Along Mini-Scan

The scanning mode includes the case when X or Y is systematically increased or decreased over time, so as to scan the beam over a range of locations. As with the pointing mode where Z≠0, the mini-scan appears as a vector on the graphical plots. However, in contrast to the pointing mode mini-scan, the vector contains a differential mode component in scanning mode and so will not lie exactly along a common mode line. Nevertheless, the same principles apply.

Once the desired mini-scan is defined (typically in terms of a reference position that lies along the mini-scan, typically the centre point of the mini-scan, and a mini-scan gradient defined by the scan speed and the value of Z at which the scan will be performed), a common mode line may be identified for the reference point. This is typically achieved using the known equations. The point along this common mode line of highest efficiency can be identified (as shown in FIGS. 11 and 12 for the pointing mode) and this frequency pair can be used as the reference point (e.g. the centre point) of any mini scan. The start and end frequency pairs to use can be derived from knowledge of the mini-scan gradient, by drawing a line of the correct gradient through the identified reference point.

For example, suppose it is desired to perform a mini-scan from point A at (X1, Z1) to point B at (X2, Z1). The value X1 will correspond to one of the common mode lines of FIG. 15, in this case the line identified as line 51. The value X2 corresponds to line 52 in FIG. 15. The value Z1 and the desired angular scan rate fixes the slope of the path line 53 shown in FIG. 15.

Accordingly, there is a choice as to the frequencies at which to start the mini-scan. In general, any pair of frequencies lying along the line 51 may be chosen as the start frequencies.

This strategy for improving the scan requires that the frequencies used at the centre of the scan have the highest possible efficiency of the options available.

To calculate this, the common mode line that is exactly in between lines 51 and 52 is identified, here shown as line 54 in FIG. 15. The point of maximum efficiency along this line is then identified and is shown at 55 in FIG. 15.

The mini-scan 53 can then be fitted to these constraints to ensure that the mini-scan 53 has this point 55 at its centre. This therefore establishes frequency pair 56 to use as the start frequency pair and pair 57 to use as the end frequency pair.

This strategy ensures that the mini-scan uses the pair of frequencies giving maximum possible efficiency at a point 55 along the mini-scan 53, preferably the centre of the mini-scan. As the efficiency map of FIG. 15 has a series of hills and valleys, with efficiency rising and falling, this strategy identifies a hill peak and puts that at the centre of the mini-scan. This means the brightest possible image is obtained.

This strategy also helps to minimise the variation in efficiency from voxel to voxel within each mini-scan. The strategy tends to ensure that a high efficiency cluster of frequencies is identified and used in the mini-scan.

The two look-up table methods can equally be used as described above, but using the reference location 55 (the location in space at some point along the mini-scan, preferably the centre) instead of the desired pointing location.

D. Minimum Threshold for Mini-Scan

A second strategy for mini-scanning is to identify the longest mini-scan line that can be drawn from the start point, at the correct gradient, that gives an unbroken efficiency above a certain threshold for the entire mini-scan. This helps to maximise mini-scan length (therefore reducing the amount of AOD resetting needed, thereby avoiding downtime associated with AOD filling) and also serves to reduce patternation by reducing the efficiency variations that can take place. This is explained with reference to FIG. 16.

With knowledge of X1 (defining the start point common mode line) and Z1 (defining the scan line gradient in FIG. 16), one can compute the longest line that it is possible to draw that passes only over areas of FIG. 16 where the efficiency is above the minimum threshold.

For example, a threshold of 30% can be set. Suppose the scan start position means that the scan must start from common mode line 192 in FIG. 16. The Z-plane and scan speed give a gradient as shown by vector 193 in FIG. 16. The longest unbroken line that can be drawn over an area where efficiency is equal to or more than 30% is shown as line 193 in FIG. 16. The whole line 193 lies over regions of FIG. 16 where efficiency is above some minimum threshold, here 30%.

The minimum threshold can be any suitable value, typically in the range 10% to 90%, optionally, 20% to 80%, or 30% to 70%, or 40% to 60%, or 50%.

In this method, the reference point for the scan path is preferably selected to be the scan start position. This establishes the common mode line for the start position in FIG. 16. The drive frequencies for the start position can be obtained by noting where the common mode line intersects with the efficiency=30% contour, shown as point 194 in FIG. 16. The line 193 is then extended until it reaches an area of FIG. 16 where efficiency starts to fall below 30%. This gives the end point drive frequencies, labelled 195 in FIG. 16.

In practice, the intersection of the efficiency=30% contour and the common mode line 192 can be obtained by identifying several candidate drive frequency pairs along the common mode line and selecting the frequency pair that has an associated efficiency above 30%, but also being the pair that has an efficiency closest to 30%.

Another method is to draw scan path lines for each of the candidate drive frequencies, ending the lines when efficiency reduces to 30% or less, and then compare each line to select the longest line.

E. Limit Variation of Efficiency Over Scan Length

The third strategy limits by how much the efficiency can change over the scan path. This helps reduce patternation considerably, because it effectively limits the range of brightnesses available in the final image.

An example is described with reference to FIG. 17. Suppose a scan is needed from common mode line 80 to common mode line 82 shown in FIG. 17. A scan passing through the point of highest possible efficiency is shown as line 84. However, it is notable here that the efficiency varies greatly along the line, from about 25% at the start, up to 100% near the centre and then to 42% at the end. Accordingly, the resulting image will have severe patternation, because the brightness will vary between 25% and 100% over the scan.

The algorithm could instead find the line in FIG. 17 that starts from the required start point common mode line 80, finishes at the required end point common mode line 82, has the gradient required by the Z focusing and scan speed constraint and which has a variation in efficiency along its length that does not exceed a maximum threshold value, say 30%. Such a line is shown as line 86, which starts at a frequency pair having 50% efficiency and ends at a point having an efficiency of 50%, with efficiency rising to be about 65% part way along the mini-scan. As such, the variation along the line is therefore only 15%, reducing patternation in the final image.

This strategy can be implemented by use of an algorithm that searches along the group of frequency pairs for the longest continuous sets of pairs that have a highest to lowest efficiency ratio that does not exceed a predetermined threshold for the duration of the scan. In the above example the highest efficiency is 65% and the lowest is 50% and so the highest to lowest efficiency ratio is 65/50=1.3. Accordingly, this scan satisfies a requirement of a highest to lowest efficiency ratio that does not exceed 2.

It should be noted that in order to minimise the number of repetitive calculations to be carried out for computing the optimum pairs of drive frequencies for many mini-scans, well known strategies and approximations may be employed that give approximately the same results as the method described here. For instance the mini-scans may be grouped into areas such as tiles that are sufficiently close to one another that only a small error in optimum common mode offset frequency results from using a single optimisation calculation for the middle voxel positioned at the centre of the tile as illustrated in FIG. 18. here there is illustrated one Z-plane showing the entire X-Y field of view 120 split into 16 tiles 122. Each tile has a centre position 124 and data of preferred frequency pairs or of common mode offset is stored for both X and Y for each tile. In the FIG. 18 example, this means storing one preferred pair or offset for each of the 4 possible X deflections and another preferred pair or offset for each of the four possible Y deflections, thereby requiring 8 storage events in total.

Additionally, the results of the optimum common mode offset calculation that is carried out only once for every tile or even every mini-scan can, as described above, be stored in a coordinate based look up table for subsequent reuse of the data. This avoids repetition of the more complex optimisation and peak efficiency finding algorithm each time it is necessary to compute the drive frequencies for a particular mini-scan or group of nearby mini-scans.

The invention also includes a method and apparatus for compiling the look-up table that can be used when configuring the acousto-optic lens.

According to this aspect, data useful for configuring the acousto-optic lens is obtained and stored, preferably in computer readable format.

Firstly, a plurality of possible locations in space that a beam of electromagnetic radiation can be deflected toward using the acousto-optic lens are defined. This will typically be a matrix of locations spanning the possible scan volume. Then, for each of the possible locations in space, a group comprising a plurality of pairs of candidate drive frequencies is identified. This group can be obtained in a similar way to the real time mode discussed above, for example 20 or so candidate drive frequency pairs may be identified. As described above, each pair of candidate drive frequencies consists of a first candidate drive frequency for said first acousto-optic deflector and a second candidate drive frequency for said second acousto-optic deflector, the pairs being such that if said first and second candidate drive frequencies of the pair were applied at the same time to the respective first and second acousto-optic deflectors, said beam of electromagnetic radiation would point toward said possible location in space. Therefore, the data so far comprises, for each of several locations in space, a group of possible frequency pairs that might be used to point the beam at that location.

Next, the efficiency of transmission of the AOL is evaluated for each of the identified candidate frequency pairs of each group. This is preferably done by actually driving the AOL with each pair of candidate frequencies and measuring the efficiency of transmission at the associated point in space. However, it could instead be done by referring to detailed data, such as the data shown in FIG. 9 and other Figures, interpolating where necessary.

Lastly, a pair of candidate drive frequencies are selected from each group. Such selection is preferably in accordance with the determined efficiency for each pair of candidate drive frequencies. Typically, the candidate pair having the best efficiency in the group are selected.

This selected candidate pair can then be stored as the preferred drive frequency for the particular possible position in space. Alternatively, a common mode frequency offset value can be determined, which, as discussed above, is a value that describes how far away from the central; differential mode line the preferred frequency pair is. This offset data is therefore data relating to the preferred frequency pair. Other data relating to the preferred frequency pair may be saved, such as offset data based on a different coordinate system or origin.

What results is a series of data (preferably in tabular format) that describes the efficiency of the AOL system in a useful way, because it allows the AOL device to be rapidly configured to optimise efficiency in use without taking too much processing power.

As an alternative to the above, the AOL controller can be provided with detailed efficiency data, such as that shown in FIGS. 9 and 10, and this data can be consulted in real time as decisions about the drive frequencies to use for a point or scan are made.

The progress made towards reducing the patternation problem and towards significantly increasing the field of view is illustrated in FIGS. 19 and 20.

FIGS. 19 and 20 give a comparison of field of view beneath a 40× NA=0.8 objective using a AFL (absolute frequency limit) scan algorithm (FIG. 19) with s=6 mrad and an OFL (optimised frequency limit) scan algorithm (FIG. 20), with a programmed semiscan angle of 6 mrad. The X-Y field of view in each image is ~180 µm (the electron microscope grid is 42 µm pitch).

Figure 3:
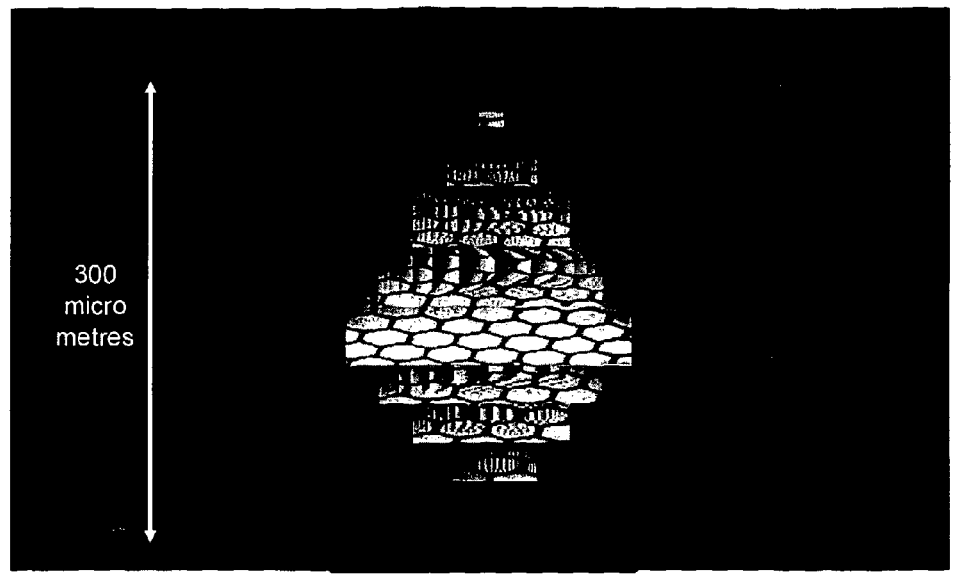
FIG. 3 shows images obtained with the prior art microscope and the patternation effect resulting from mini-scans at planes where $Z \neq 0$.

FIG. 19 shows what happens if the semiscan angle, s, is increased to 6 mrad in order to increase the field of view beneath an NA=0.8, 40× objective using the AFL algorithm. The characteristic programmed octahedral shape can be seen with very small scan area at large Z displacements in order to avoid the AODs going beyond their frequency limits. Note that the patternation in this image is much more pronounced than in FIG. 3, because s=6 mrad rather than 4.3 mrad so the AODs in each mini-scan are allowed to scan a larger frequency range. At both ends of each mini-scan for Z=+37.5 µm and −42.5 µm the intensity of the 2-photon image drops significantly.

The results of the new OFL (Optimised frequency limit) algorithm set for the same XY scan coverage are shown in FIG. 20. Note that the OFL scan algorithm is showing approximately constant scan area and clear images of the EM grid over a ~160 µm axial range. The fading of intensity at the edges of the field of view is presumably caused by the severe chromatic aberration at these large X-Y deflections as well as reductions in the AOL efficiency. However, it is clear that good progress has been made in both extending field of view and in reducing patternation.

The slight tartan pattern on the image of FIG. 20 is caused by the fact that no drive amplitude or Pockel's cell compensation to the change in efficiency which occurs when the algorithm jumps from one high efficiency maximum to another was used. Similarly no attempt has been made to compensate for changes in efficiency across the field of view caused by variation in peak efficiency of each mini-scan. Such refinements can be added later.

As shown by comparing FIGS. 19 and 20, the field of view for the OFL algorithm compared to the AFL algorithm, for the same scan dimensions at Z=0 is cuboid rather than octahedral and thus has an approximately 3 times larger scan volume depending precisely on the limits to Z scan caused for instance by loss of resolution. This larger cubic field of view and reduced patternation is clearly a very significant step forward.

The invention claimed is:

1. A method of configuring an acousto-optic lens for manipulating a beam of electromagnetic radiation so as to be deflected and focused toward a desired location in space, said acousto-optic lens comprising at least a first acousto-optic deflector driven by a first drive frequency and a second acousto-optic deflector driven by a second drive frequency, said method comprising:

for each of a plurality of possible locations in space, separately storing data related to a preferred frequency pair, wherein a preferred frequency pair for a first one of said possible locations in space consists of a first preferred drive frequency for said first acousto-optic deflector and a second preferred drive frequency for said second acousto-optic deflector, said preferred frequency pair being such that if said first and second preferred drive frequencies of said pair were applied at the same time to said respective first and second acousto-optic deflectors, said beam of electromagnetic radiation would be deflected toward said first one of said possible locations in space;

consulting said data to determine a preferred frequency pair based on said desired location in space;

determining first and second drive frequencies as a result of said consulting step.

2. The method of claim 1, wherein said stored data comprises frequency modification data and wherein consulting said data comprises:
- determining a pair of reference frequencies for said desired location in space, said pair of reference frequencies being such that if the reference frequencies of said pair were applied to said respective first and second acousto-optic deflectors, said beam of electromagnetic radiation would be deflected toward said desired location in space;
- consulting the stored data to obtain frequency modification data; and
- modifying said pair of reference frequencies according to said frequency modification data to obtain said preferred frequency pair.

3. The method of claim 1, wherein determining the first and second drive frequencies comprises setting said first and second drive frequencies to be respectively equal to said first and second preferred drive frequencies of the preferred frequency pair.

4. The method of claim 1, wherein consulting said data comprises identifying the data stored for the possible location that is closest to said desired location and determining that that data relates to the preferred frequency pair for said desired location in space.

5. The method of claim 4, wherein determining the first and second drive frequencies comprises:
- modifying said preferred frequency pair so as to obtain a drive frequency pair such that if the drive frequencies of said drive frequency pair were applied to said respective first and second acousto-optic deflectors, said beam of electromagnetic radiation would be deflected toward said desired location in space.

6. The method of claim 1, wherein said acousto-optic lens additionally comprises a third acousto-optic deflector driven by a third drive frequency and a fourth acousto-optic deflector driven by a fourth drive frequency;
- said method additionally comprising:
  - for each of said plurality of possible locations in space, storing data related to a second preferred frequency pair, wherein a second preferred frequency pair for a second one of said possible locations in space consists of a third preferred drive frequency for said third acousto-optic deflector and a fourth preferred drive frequency for said fourth acousto-optic deflector, said second preferred frequency pair being such that if said third and fourth preferred drive frequencies of said second pair were applied at the same time to said respective third and fourth acousto-optic deflectors, said beam of electromagnetic radiation would be deflected toward said second one of said possible locations in space;
  - consulting said data to determine a second preferred frequency pair based on said desired or reference location;
  - determining third and fourth drive frequencies as a result of said consulting step.

7. An apparatus for controlling an acousto-optic lens for manipulating a beam of electromagnetic radiation so as to be deflected and focused toward a desired location in space, said acousto-optic lens comprising at least a first acousto-optic deflector driven by a first drive frequency and a second acousto-optic deflector driven by a second drive frequency, said apparatus comprising:
- a memory configured to separately store, for each of a plurality of possible locations in space, data related to a preferred frequency pair, wherein a preferred frequency pair for a first one of said possible locations in space consists of a first preferred drive frequency for said first acousto-optic deflector and a second preferred drive frequency for said second acousto-optic deflector, said preferred frequency pair being such that if said first and second preferred drive frequencies of said pair were applied at the same time to said respective first and second acousto-optic deflectors, said beam of electromagnetic radiation would be deflected toward said first one of said possible locations in space;
- a controller configured to consult said data to determine a preferred frequency pair based on said desired location in space;
- said controller being configured to determine first and second drive frequencies as a result of said consulting.

8. The apparatus of claim 7, wherein said memory is configured to store data that comprises frequency modification data and wherein said controller is configured to:
- determine a pair of reference frequencies for said desired location in space, said pair of reference frequencies being such that if the reference frequencies of said pair were applied to said respective first and second acousto-optic deflectors, said beam of electromagnetic radiation would be deflected toward said desired location in space;
- consult the stored data to obtain frequency modification data; and
- modify said pair of reference frequencies according to said frequency modification data to obtain said preferred frequency pair.

9. The apparatus according claim 7, wherein said acousto-optic lens additionally comprises a third acousto-optic deflector driven by a third drive frequency and a fourth acousto-optic deflector driven by a fourth drive frequency;
- said memory being configured to additionally store for each of said plurality of possible locations in space, data related to a second preferred frequency pair, wherein a second preferred frequency pair for a second one of said possible locations in space consists of a third preferred drive frequency for said third acousto-optic deflector and a fourth preferred drive frequency for said fourth acousto-optic deflector, said second preferred frequency pair being such that if said third and fourth preferred drive frequencies of said second pair were applied at the same time to said respective third and fourth acousto-optic deflectors, said beam of electromagnetic radiation would be deflected toward said second one of said possible locations in space;
- said controller being configured to consult said data to determine a second preferred frequency pair based on said desired or reference location;
- said controller being configured to determine third and fourth drive frequencies as a result of said consulting.

10. A microscope for deflecting a beam of electromagnetic radiation toward a desired location in space, said microscope comprising:
- an acousto-optic lens comprising at least a first acousto-optic deflector driven by a first drive frequency and a second acousto-optic deflector driven by a second drive frequency;
- the apparatus of claim 7 to control said acousto-optic lens;
- microscope optics;
- a laser for supplying said beam of electromagnetic radiation;
- wherein said controller is configured to:
- apply said first drive frequency to said first acousto-optic deflector;
- simultaneously apply said second drive frequency to said second acousto-optic deflector; and simultaneously cause said laser to supply said beam of electromagnetic radiation to the input aperture of said first acousto-optic deflector.

11. A method of preparing data useful for configuring an acousto-optic lens, said method comprising:
- selecting a plurality of possible locations in space that a beam of electromagnetic radiation can be deflected toward using the acousto-optic lens;
- determining, for each of said possible locations in space, a group comprising a plurality of pairs of candidate drive frequencies, each pair of candidate drive frequencies consisting of a first candidate drive frequency for said first acousto-optic deflector and a second candidate drive frequency for said second acousto-optic deflector, said pairs being such that if said first and second candidate drive frequencies of said pair were applied at the same time to said respective first and second acousto-optic deflectors, said beam of electromagnetic radiation would point toward said possible location in space;
- determining, for each pair of candidate drive frequencies in said group, an efficiency of transmission of said beam of electromagnetic radiation through said acousto-optic lens; and
- selecting as preferred a pair of candidate drive frequencies from said group in accordance with the determined efficiency for each pair of candidate drive frequencies.

12. A method of configuring an acousto-optic lens for manipulating a beam of electromagnetic radiation so as to point at a desired location in space, said acousto-optic lens comprising at least a first acousto-optic deflector driven by a first drive frequency and a second acousto-optic deflector driven by a second drive frequency, said method comprising:
- determining a group comprising a plurality of pairs of candidate drive frequencies, each pair of candidate drive frequencies consisting of a first candidate drive frequency for said first acousto-optic deflector and a second candidate drive frequency for said second acousto-optic deflector, said pairs being such that if said first and second candidate drive frequencies of said pair were applied at the same time to said respective first and second acousto-optic deflectors, said beam of electromagnetic radiation would point at said desired location in space;
- determining, for each pair of candidate drive frequencies in said group, an efficiency of transmission of said beam of electromagnetic radiation through said acousto-optic lens; and
- selecting a pair of candidate drive frequencies from said group in accordance with the determined efficiency for each pair of candidate drive frequencies.

* * * * *